(12) United States Patent
Cunningham et al.

(10) Patent No.: US 7,531,786 B2
(45) Date of Patent: May 12, 2009

(54) PHOTONIC CRYSTAL SENSORS WITH INTEGRATED FLUID CONTAINMENT STRUCTURE

(75) Inventors: Brian T. Cunningham, Champaign, IL (US); Charles Choi, Savoy, IL (US)

(73) Assignee: The Board of Trustees of the Universiy of Illinois, Urbana, IL (US)

( * ) Notice: Subject to any disclaimer, the term of this patent is extended or adjusted under 35 U.S.C. 154(b) by 55 days.

(21) Appl. No.: 11/983,108

(22) Filed: Nov. 6, 2007

(65) Prior Publication Data

US 2008/0265137 A1    Oct. 30, 2008

Related U.S. Application Data

(60) Provisional application No. 60/865,093, filed on Nov. 9, 2006.

(51) Int. Cl.
*H01L 31/00* (2006.01)
(52) U.S. Cl. ..................... 250/214.1; 250/239
(58) Field of Classification Search .............. 250/214.1, 250/239, 573; 385/12–14; 264/437–440, 264/108, 313; 356/437
See application file for complete search history.

(56) References Cited

U.S. PATENT DOCUMENTS

| | | | | |
|---|---|---|---|---|
| 6,685,870 B2 * | 2/2004 | Ukechi et al. | ............... | 264/437 |
| 6,990,259 B2 | 1/2006 | Cunningham | ................ | 385/12 |
| 7,023,544 B2 | 4/2006 | Cunningham et al. | ....... | 356/326 |
| 7,094,595 B2 | 8/2006 | Cunningham et al. | .... | 435/287.2 |
| 7,118,710 B2 | 10/2006 | Cunningham | ............ | 422/82.09 |
| 7,157,053 B2 | 1/2007 | Hahn et al. | .............. | 422/82.09 |
| 7,171,095 B2 | 1/2007 | Sugita et al. | ................. | 385/129 |
| 7,391,945 B2 | 6/2008 | Sugita | ........................ | 385/122 |
| 7,412,938 B2 | 8/2008 | Hodes et al. | ............... | 114/67 R |
| 7,444,053 B2 | 10/2008 | Schmidt et al. | ............. | 385/129 |

OTHER PUBLICATIONS

Office Action dated Dec. 24, 2008 in U.S. Appl. No. 11/983,109, filed Nov. 6, 2007.
Birner et al., *Silicon-based Photonic Crystals*, Advanced Materials, vol. 13, No. 6, pp. 377-388 (2001).
Cunningham et al., *Colorimetric Resonant Reflection as a Direct Biochemical Assay Technique*, Sensors and Actuators B, 4120, pp. 1-13 (2001).
Cunningham et al., *A Plastic Colorimetric Resonant Optical Biosensor for Multi-parallel Detection of Label Free Biochemical Interactions*, Sensors and Actuators B 4283, vol. 85, pp. 1-8 (2002).

(Continued)

*Primary Examiner*—Que T Le
(74) *Attorney, Agent, or Firm*—McDonnell Boehnen Hulbert & Berghoff LLP

(57) ABSTRACT

Photonic crystal (PC) sensors, and sensor arrays and sensing systems incorporating PC sensors are described which have integrated fluid containment and/or fluid handling structures. Sensors and sensing systems of the present disclosure are capable of high throughput sensing of analytes in fluid samples, bulk refractive index detection, and label-free detection of a range of molecules, including biomolecules and therapeutic candidates. The present disclosure also provides a commercially attractive fabrication platform for making photonic crystal sensors and systems wherein an integrated fluid containment structure and a photonic crystal structure are fabricated in a single molding or imprinting processing step amendable to high throughput processing.

7 Claims, 16 Drawing Sheets

OTHER PUBLICATIONS

U.S. Appl. No. 11/983,109, Brian T. Cunningham, filed Nov. 6, 2007.
International Search Report and Written Opinion mailed Apr. 10, 2008 in PCT/US2007/023408, filed Nov. 6, 2007.

Choi et al., *Single-step fabrication and characterization of photonic crystal biosensors with polymer microfluidic channels*, The Royal Society of Chemistry 2006, Lab on a Chip 2006 vol. 6, pp. 1373-1380 (2006).

* cited by examiner

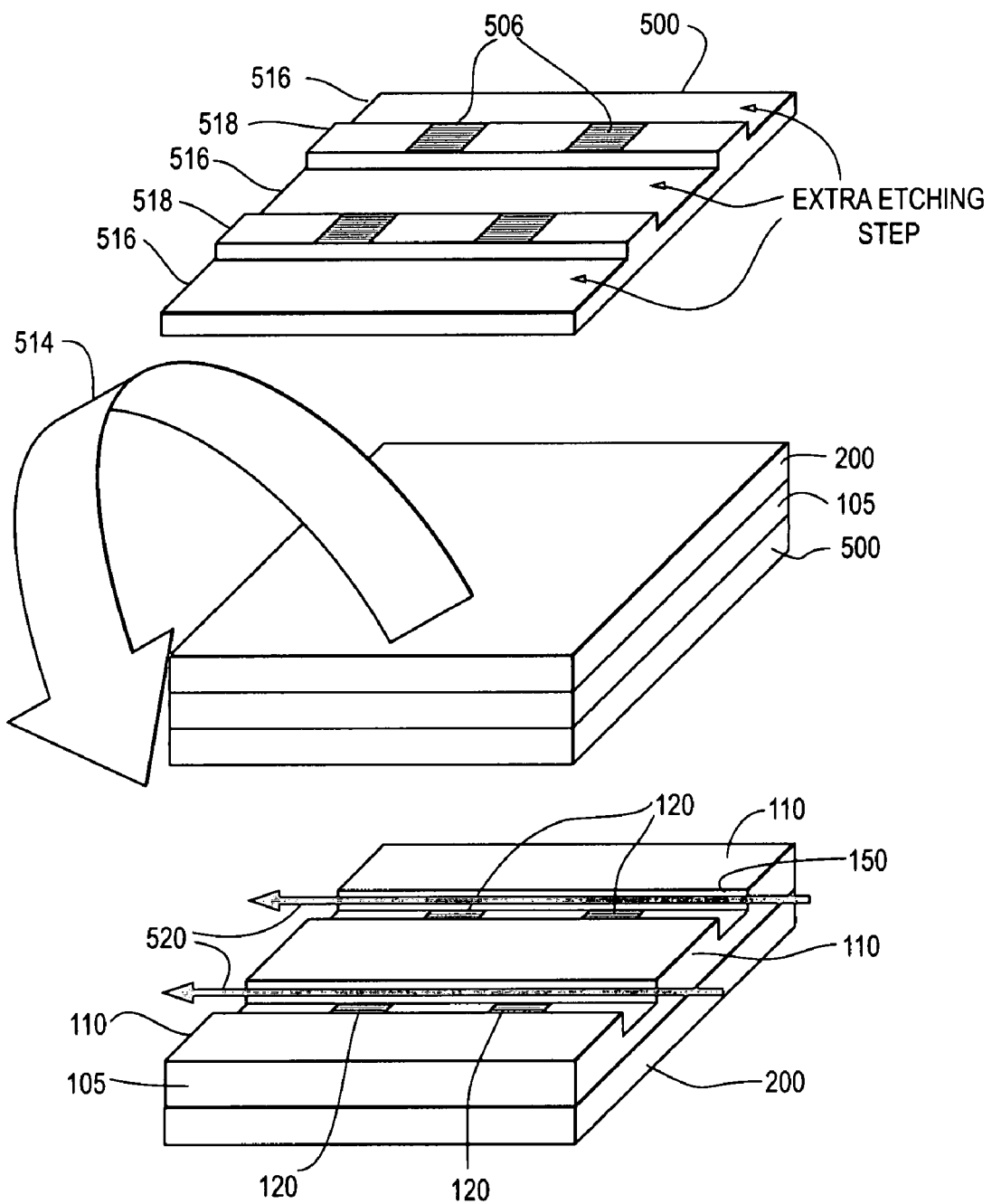

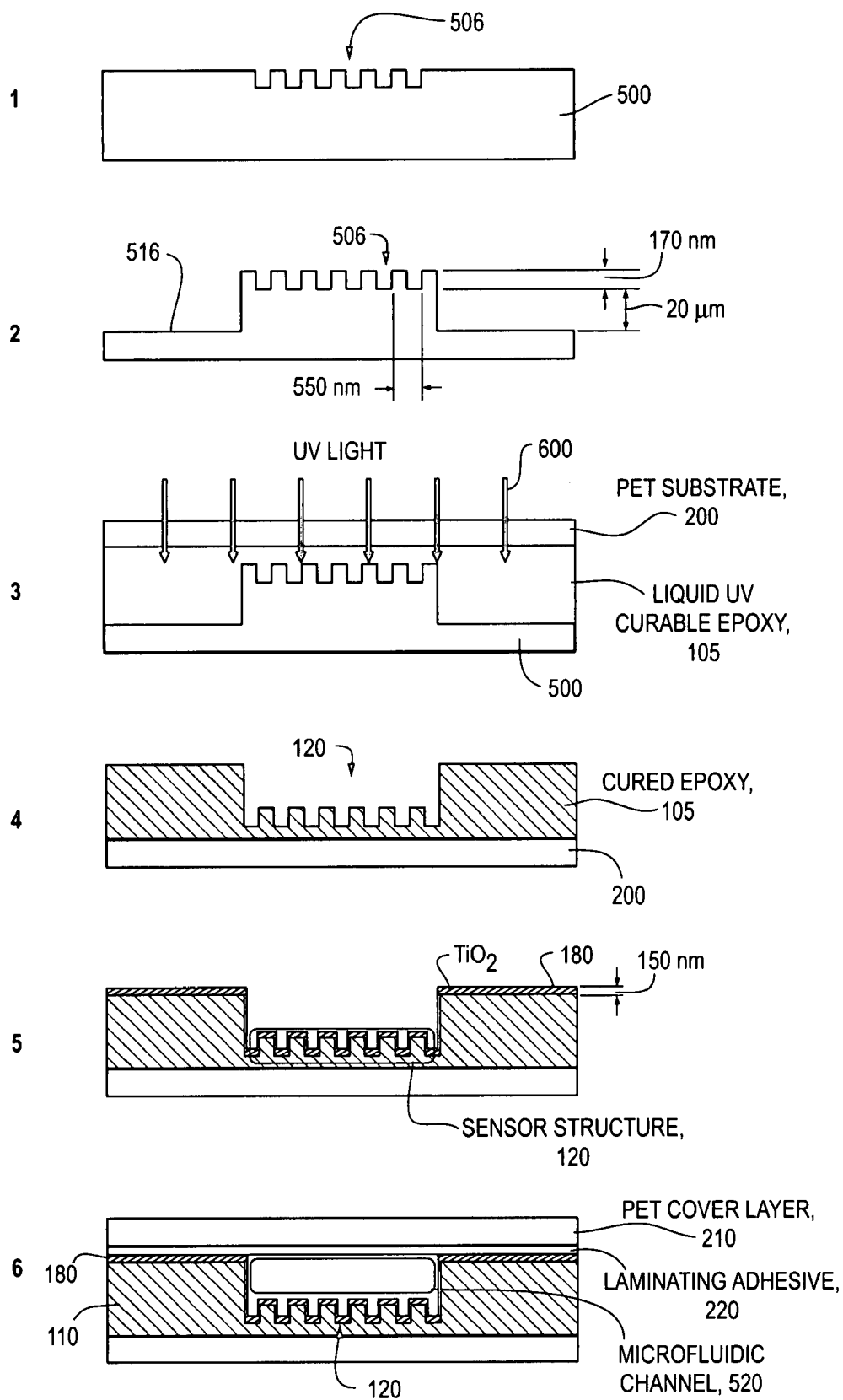

US 7,531,786 B2

PHOTONIC CRYSTAL SENSORS WITH INTEGRATED FLUID CONTAINMENT STRUCTURE

CROSS REFERENCE TO RELATED APPLICATIONS

Pursuant to the provisions of 35 U.S.C. § 119 (e), this application claims priority to U.S. Provisional Application Ser. No. 60/865,093 filed Nov. 9, 2006, the content of which is incorporated by reference herein.

STATEMENT REGARDING FEDERALLY SPONSORED RESEARCH OR DEVELOPMENT

This invention was made, at least in part, with United States governmental support awarded by National Science Foundation under NSF DM1 03-28162. The United States Government has certain rights in this invention.

BACKGROUND OF DISCLOSURE

Photonic crystals, also commonly referred to as photonic bandgap structures, are periodic dielectric or metallic structures exhibiting a spatially periodic variation in refractive index that forbids propagation of certain frequencies of incident electromagnetic radiation. The photonic band gap of a photonic crystal refers to the range of frequencies of electromagnetic radiation for which propagation through the structure is prevented. The photonic band gap phenomenon may be conceptualized as complete reflection of incident electromagnetic radiation having selected frequencies due to interaction with the periodic structural domains of a photonic crystal. The spatial arrangement and refractive indices of these structural domains generate photonic bands gaps that inhibit propagation of electromagnetic radiation centered about a particular frequency. Background information on photonic crystals include the following references: (1) Joanopoulus et al., "Photonic Crystals Molding the Flow of Light", Princeton University Press, 1995; (2) A. Birner, et al., "Silicon-Based Photonic Crystals", Advanced Materials, Volume 13, Issue 6, Pages 377-388; and (3) Steven G. Johnson, and John D. Joannopoulos, "Photonic Crystals: The Road from Theory to Practice", Springer, 2002.

Photonic crystals provide an electromagnetic analog to electron-wave behavior observed in crystals wherein electron-wave concepts, such as dispersion relations, Bloch wave functions, van Hove singularities and tunneling, having electromagnetic counterparts in photonic crystals. In semiconductor crystals, for example, an electronic band gap of energy states for which electrons are forbidden results from a periodic atomic crystalline structure. By analogy, in a photonic crystal, a photonic band gap of forbidden energies (or wavelengths/frequencies) of electromagnetic radiation results from a periodic structure of a dielectric material where the periodicity is of a distance suitable to interact with incident electromagnetic radiation.

Selection of the physical dimensions, refractive indices and spatial distribution of periodic structural components ("surface grating" herein) of a photonic crystal provides an effective means of designing a photonic crystal a photonic band gap with a selected frequency distribution. If the periodicity and symmetry of the crystal and the dielectric constants of the materials used are chosen appropriately, the photonic crystal will selectively couple energy at particular wavelengths, while excluding others. One-dimensional, two-dimensional and three-dimensional photonic crystals have been fabricated providing complete or at least partial photonic band having selected frequency distributions gaps in one or more directions. Photonic crystals have also been fabricated having selected local disruptions (e.g., missing or differently-shaped portions of the structural domains of periodic array) in their periodic structure, thereby generating defect or cavity modes with frequencies within a forbidden bandgap of the crystal. Photonic crystals having specific defects are of particular interest because they provide optical properties useful for controlling and manipulating electromagnetic radiation, such as the ability to provide optical confinement and/or wave guiding with very little, or substantially no, radiative losses. U.S. Pat. No. 6,990,259 to Cunningham describes a "defect" biosensor in greater detail. The content of the '259 patent is incorporated by reference herein.

As diffraction and optical interference processes give rise to the photonic band gap phenomenon, the periodicity of photonic crystal structures is typically on the order of the wavelength of incident electromagnetic radiation. Accordingly, photonic crystals for controlling and manipulating visible and ultraviolet electromagnetic radiation typically comprise dielectric or metallic structures with periodic structural domains having submicron physical dimensions on the order of 100's of nanometers. A number of fabrication pathways for making periodic structures having these physical dimensions have been developed over the last decade, including micromachining and nanomachining techniques (e.g., lithographic patterning and dry/wet etching, electrochemical processing etc.), colloidal self assembly, replica molding, layer by-layer assembly and interference lithography. Advances in these fabrication techniques have enabled fabrication of one-dimensional, two-dimensional and three-dimensional photonic crystals from a range of materials including dielectric crystals, metals, polymers and colloidal materials.

The applications of photonic crystal sensors are numerous, including integration with lasers to inhibit or enhance spontaneous emission, waveguide angle steering devices, and as narrowband optical filters. A photonic crystal structure geometry can be designed to concentrate light into extremely small volumes and to obtain very high local electromagnetic field intensities.

In order to adapt a photonic crystal device to perform as a biosensor, some portion of the structure must be in contact with a test sample. By attaching biomolecules or cells to the portion of the photonic crystal where the locally confined electromagnetic field intensity is greatest, the resonant coupling of light into the crystal is modified, so the reflected/transmitted output is tuned. The highly confined electromagnetic field within a photonic crystal structure provides high sensitivity and a high degree of spatial resolution consistent with their use in imaging applications, much like fluorescent imaging scanners.

For example, photonic crystals with subwavelength periodic grating structures have been developed to reflect only a very narrow band of wavelengths when illuminated with white light. To create a biosensor, a photonic crystal may be optimized to provide an extremely narrow resonant mode whose wavelength is particularly sensitive to modulations (i.e., shifts) induced by the deposition of biochemical material on its surface. In typical practice, a photonic crystal sensor consists of a low refractive index plastic material with a periodic surface structure that is coated with a thin layer of high refractive index dielectric material. The sensor is measured by illuminating the surface with white light, and collecting the reflected light with a non-contact optical fiber probe, where several parallel probes can be used to independently measure shifts in the peak wavelength of reflected light ("PWV") at different locations on the sensor. The biosensor design enables a simple manufacturing process to produce sensor sheets in continuous rolls of plastic film that are hundreds of meters in length. The mass manufacturing of a biosensor structure that is measurable in a non-contact mode over large areas enables the sensor to be incorporated into single-use disposable consumable items such as 96, 384, and 1536-well standard microplates, thereby making the sensor compatible with standard fluid handling infrastructure employed in most laboratories. In these cases, the photonic crystal is manufactured in separate manufacturing operation, and then, in a second step, glued or otherwise adhered to a bottomless microplate. The wells of the microplates provide a reservoir by which a fluid sample can be introduced onto the photonic crystal surface.

The sensor operates by measuring changes (shifts) in the wavelength of reflected light ("PWV") as biochemical binding events take place on the surface. For example, when a protein is immobilized on the sensor surface, an increase in the reflected wavelength is measured when a complementary binding protein is exposed to the sensor. Using low-cost components, the readout instrument is able to resolve protein mass changes on the surface with resolution less than 1 $pg/mm^2$. While this level of resolution is sufficient for measuring small-molecule interactions with immobilized proteins, the dynamic range of the sensor is large enough to also measure larger biochemical entities including live cells, cell membranes, viruses, and bacteria. A sensor measurement requires about 20 milliseconds, so large numbers of interactions can be measured in parallel, and kinetic information can be gathered. The reflected wavelength of the sensor can be measured either in "single point mode" (such as for measuring a single interaction within a microplate), or an imaging system can be used to generate an image of a sensor surface with <9 μm resolution. The "imaging mode" has been used for applications that increase the overall resolution and throughput of the system such as label-free microarrays, imaging plate reading, self-referencing microplates, and multiplexed spots/well.

Given substantial advances in their fabrication and their unique optical properties, photonic crystal-based sensors have been recently developed for a range of biosensing applications. To operate as a biosensor, a photonic crystal is provided in a configuration such that its active area is exposed to a fluid containing analytes for detection. The presence of analyte proximate to the photonic crystal sensor modulates the resonant coupling of light into the crystal, thereby resulting in a measurable change in the wavelength distribution of electromagnetic radiation transmitted, scattered or reflected by the crystal resulting from changes in the photonic band gap of the crystal. The highly localized nature of the confined electromagnetic field generated by the crystal ensures that that detection via photonic crystal based sensors is restricted to a probe region proximate to (e.g., 100-400 nanometers) the active area of the sensor. In typical sensing applications, a read out system is used wherein polarized electromagnetic radiation having a selected wavelength distribution is provided to the photonic crystal and subsequently reflected or transmitted electromagnetic radiation is frequency analyzed by an appropriate photodetector, such as a spectrometer in combination with an appropriate detector. By observing and/or quantifying the change in wavelength distribution resulting from interaction of the fluid and the photonic crystal, analytes in the probe region are detected and/or analyzed.

Biosensors incorporating photonic crystal structures are described in the following references which are hereby incorporate by reference: U.S. Pat. Nos. 7,118,710, 7,094,595, 7,023,544, and 6,990,259; and Cunningham, B. T., P. Li, B. Lin and J. Pepper, Colorimetric Resonant Reflection as a Direct Biochemical Assay Technique, Sensor and Actuators B, 2002, 81, pgs 316-328; and Cunningham, B. T. J. Qiu, P. Li, J. Pepper and B. Hugh, A Plastic Calorimetric Resonant Optical Biosensor for Multiparallel Detection of Label 10 Free Biochemical Interactions, Sensors and Actuators B, 2002, 85, pgs 219-226.

Advantages provided by photonic crystals for biosensing include the ability to detect and characterize a wide range of materials, including peptides, proteins, oligonucleotides, cells, bacteria and virus particles, without the use of labels, such as fluorescent labels and radioligands, or secondary reporter systems. Direct detection provided by photonic crystal sensing enhances easy of implementation of these techniques by eliminating labor intensive processing required to synthetically link and/or read out a label or reporter system. This beneficial aspect of photonic crystal-based sensing also eliminates a significant source of experimental uncertainty arising from the influence of a label or reporter system on molecular conformation, reactivity, bioactivity and/or kinetics; and eliminates problems arising from liquid phase fluorescence quenching processes. Photonic crystal based sensors are also compatible with functionalization, for example by incorporation of biomolecules and/or candidate therapeutic molecules bound to the surface of the active area of the photonic crystal structure; a capability which is particularly attractive for selectively detecting specific target molecules for screening and biosensing applications. Other benefits provided by photonic crystal approaches to biosensing include: (i) good sensitivity and image resolution; (ii) compatibility with relatively straightforward optical readout systems, (iii) and the ability to provide highly localized detection useful for multichannel systems having a high area density sensors are emerging as a major tool for selective biochemical detection and analysis in diverse fields including genomics, proteomics, pharmaceutical screening and biomedical diagnostics.

In current practice, photonic crystal biosensors and the associated larger-scale fluid containment features (such as wells or channels) are typically fabricated separately and subsequently integrated via alignment and bonding processes. Given the submicron scale of features of the photonic crystal and micron or larger scale physical dimensions of the fluid containment structures, alignment and bonding steps in photonic crystal-based sensors present significant practical challenges, and thus add to the overall cost and complexity of fabrication of these devices. First, the components of photonic crystal biosensors are optimally aligned such that the maximum extent of active area of the photonic crystal is exposed to fluid held in the fluid containment structure. Second, bonding and alignment must effectively prevent liquid from exiting a given fluid containment structure and spreading to one or more adjacent fluid containment structures in a multichannel sensor configuration. This requirement is necessary to avoid sensing interferences arising from cross talk between adjacent photonic crystal sensors. Third, the force applied to the photonic crystal structure during alignment and bond must be sufficiently low so as not to damage the nanoscale periodic features of the crystal. Damage to such features can introduce unwanted defect structures to the photonic crystal that can strongly influence sensing capabilities and readout of the device.

SUMMARY

This disclosure is premised on the inventors' insight that photonic crystal sensors are capable of integration in a monolithic device having fluid containment structures such as wells or flow channels, including arrays of wells and associated fluid flow channels. The sensors of the present disclosure have a great potential for implementation in microfluidic lab-on-a chip (LOC) devices, micro-total-analysis systems (μTAS) and biosensor—embedded microarray systems.

In these applications of the present disclosure, fluid containment structures, such as wells or fluid flow channels, are integrated with the sensor directly resulting in a monolithic, integral structure. The fluid containment structures can be designed to effectively convey the sample to the active area (periodic surface grating) of a photonic crystal. In some applications, the fluid containment structures further function in multichannel biosensor configurations to provide a fluid sample to a selected photonic crystal in a manner preventing the fluid sample spreading between adjacent sensors on the same substrate. Flow cells, such as microfluidic channels, are commonly used to provide a means for conveying a fluid sample through a narrow channel from a sample reservoir to the photonic crystal structure for analysis. Typical flow cell configurations employ an etched trench having an attached cover plate. These fluid containment and delivery systems must be precisely aligned to and effectively sealed against the photonic crystal active area so as to prevent leakage of sample. In other embodiments, the fluid containment structure is static, such as a cuvette aligned and bonded over the photonic crystal active area. In these embodiments, the photonic crystal sensor is provided as an internal surface of the cuvette. In multi-array configurations, for example, a large number of cuvettes each having an individually-addressed, independent photonic crystal sensors are provided in a microplate format, such as a 96, 384 or 1536 microarray format.

In another aspect, a biosensor is described having a integral structure having an inlet port, a plurality of sample wells connected to the inlet port, and a plurality of flow channels connecting the inlet port to the sample wells, and a plurality of photonic crystal sensors. The photonic crystal sensors are positioned in a flow channel connecting the inlet port to the sample wells. In one specific embodiment, each of the sample wells also includes a photonic crystal sensor.

The physical dimensions and shapes of the fluid containment and/or handling structures can take a variety of forms. Some forms are useful for constraining, transporting or otherwise providing a fluid sample to the photonic crystal sensor such that analytes in the sample can be effectively detected and/or analyzed. Integrated fluid containment and/or fluid handling structures of the present disclosure can also include active fluidic structures in the form of flow channels where the sample moves over the photonic crystal, such as microfluidic and nanofluidic flow channels. In other embodiments, the fluid containment structures are passive, and may take the form of cuvettes, wells and microwell arrays.

Embodiments of the present disclosure include fluid containment structures which are oriented in a substantially aligned configuration. For example, in an embodiment in which the fluid containment structures include a multitude of channels each having a photonic crystal formed at the bottom of the channel, the photonic crystals in the various channels are aligned with each other, i.e., in a straight line. As such, measurements of all the photonic crystal sensors can be made simultaneously in a line-scanning type imaging spectrometer detection apparatus. The alignment is deterministically selected and controlled during fabrication. The resulting biosensor provides good image resolution, high sensitivities and detection efficiencies.

The biosensors and associated detection instruments of the present disclosure are capable of high throughput sensing of analytes in fluid samples, bulk refractive index detection, and label-free detection of a range of molecules, including biomolecules and therapeutic candidates. The biosensors and associated detection instruments also provide imaging functionality wherein a spatial profile of the active area of a photonic crystal sensor or array of photonic crystal sensors is characterized with good resolution and sensitivity. This functionality is particularly useful, for example, for providing imaging assays within a fluidic channel or for reading out a plurality of microwells provided in a microarray configuration.

The present disclosure also features commercially attractive fabrication methods for making photonic crystal sensors, sensor arrays and systems with integrated fluid containment structures. The fabrication methods of the present disclosure are capable of cost effective and high throughput implementation for the manufacture of photonic crystal sensors, including polymer-based photonic crystal sensors. Some methods of this aspect of the present disclosure use a processing strategy wherein an integrated fluid containment structure and a photonic crystal structure are fabricated simultaneously via single step integration, amendable to high throughput processing. Useful processing methods of this aspect of the present disclosure include the use of replica molding and imprint lithography techniques. The methods enable automatic, high precision alignment of both the photonic crystal sensors and the fluid containment structures so as to ensure high performance device functionality. The present fabrication methods are particularly well suited for making photonic crystal sensors comprising polymer materials, including mechanically flexible polymer based photonic crystal sensors and systems, and making arrays of photonic crystal sensors covering large areas, and optionally, provided in a dense area configurations.

In the context of this description, the expression "monolithic structure" refers to a unitary structure having a plurality of integrally connected structural elements. An exemplary monolithic structure in some embodiments comprises a plurality of integrated structural elements comprising a structurally continuous material, including a structurally continuous composite (multilayered) material. In some embodiments, the monolithic structure of sensors of the present disclosure comprise a single, continuous polymer structure wherein the surface grating structure of a photonic crystal forms part of the one internal surface of a fluid containment structure, e.g., the bottom surface of a sample well or fluid flow channel. In some embodiments, the monolithic structure comprising the integrated fluid containment and photonic crystal structures is a mechanically flexible monolithic polymer structure. In other embodiments the monolithic structure is rigid. Embodiments of the present disclosure having such a multi-component monolithic structure are useful for providing a sensor in which the periodic surface grating area of the photonic crystal is substantially aligned within a fluid containment structure, capable of providing efficient and sensitive detection and characterization of analytes. Further, such multi-component monolithic structures are useful for providing photonic crystal sensors that are not susceptible to problems associated with fluid sample leaking out of the fluid containment structure of the sensor.

In an embodiment, the monolithic structure comprising the fluid containment structure and the photonic crystal structures has discrete structural domains, one corresponding to a fluid containment structure and the other corresponding to the periodic grating structure of the photonic crystal sensor. The discrete structural domains may have substantially different physical dimensions, for example physical dimensions that differ by at least one order of magnitude, and in some embodiments physical dimensions that differ by at least two orders of magnitude. For example, the photonic crystal surface grating structure may be nano-sized features, whereas the cavity of the fluid containment structure (flow channel or well) may be a micro-sized feature. The physical dimensions and shapes of cavities of fluid containment structures of the present disclosure can vary significantly for different sensing applications. Several possibilities include fluid flow channels, cuvettes, and microwell and microarray configurations. In representative embodiments, the periodic grating is of a sub-illumination wavelength size, for example having physical dimensions selected over the range of about 20 nanometers to about 500 nanometers, whereas the fluid containment structures, such as cavities, channels and recessed or grating structures, are in the range of about 10 microns to about 1000 microns.

In an embodiment of this aspect of the present disclosure, the grating structure of the photonic crystal is provided on a bottom or internal surface of the cavity of fluid containment structure, and in a configuration wherein the grating structures extend from one side of the cavity to the other side. For example, sensors of the present disclosure include configurations wherein the fluid containment structure is a fluid flow channel having a surface grating structure extending from one side of the channel to the opposite side. The periodic surface grating can take the form of a one dimensional spatially periodic configuration such as a parallel array of alternating high and low portions. Other periodic structures are possible including two-dimensional gratings (arrays of posts or holes) or two-level, two dimensional periodic structures.

In an embodiment, the photonic crystal structure provided on the internal surface of the fluid containment structure comprises a dielectric and/or semiconductor structure having a spatial distribution of refractive indices that varies periodically in at least two dimensions. Sensors of this embodiment of the present disclosure, for example, may comprise a photonic crystal structure having a two-dimensional periodic array of alternating high refractive index elements and low refractive index elements.

In one sensor configuration, high refractive index elements, such as thin dielectric and/or semiconductor films, are disposed on top surfaces of at least a portion of the periodic surface grating and on the bottom surfaces of the grating. Thin films providing high refractive index elements useful in the present disclosure have thicknesses selected over the range of about 20 nanometers to about 500 nanometers and include, but are not limited to, $TiO_2$ films, silicon nitride, tantalum oxide, zinc sulfide, and hafnium oxide.

In the context of this description, "high refractive index elements" have a refractive index higher than "low refractive index elements", for example a refractive index at least 1.2 times larger than the low refractive index elements in some embodiments. In some sensors, the combination of high refractive index thin films provided on top of low refractive index grating structures (and optionally on side surface of grating structures) results in a photonic crystal structure having a spatial distribution of refractive indices that varies periodically in two dimensions. Sensors of the present disclosure include, additionally, photonic crystal structures having grating structures provided in a spatially periodic configuration that includes at least one defect site in a one-, two-, or three dimensional array, such as a missing relief feature(s), extra relief feature(s) or relief feature(s) having different physical dimensions. Sensors of the present disclosure can also include photonic crystal structures provided on the internal surface of the fluid containment structure comprising a three-dimensional periodic array of alternating high refractive index elements and low refractive index elements.

Sensors of the present disclosure may have a wide variety of integrated fluid containment structures, including active fluidic delivery and handling systems, passive fluid reservoirs and all combinations and arrays and systems thereof. In an embodiment, the cavity of the fluid containment structure is a fluidic channel, such as a microfluidic or nanofluidic channel. Fluidic channels useful as fluid containment structures of the present disclosure are optionally a component of an active fluidic system having pumps, valves, reservoirs and/or fluidic channel networks. In an embodiment, the cavity of the fluid containment structure is a static reservoir, such as a cuvette, microwell, microcuvette and microreservoir. Sensors of this aspect of the present disclosure may be provided in an array format wherein a plurality of fluid containment structures comprising microwells are provided in a microarray format, wherein each microwell has a photonic crystal structure provided on an internal surface.

In some embodiments of this disclosure, the sensor further includes a cover layer positioned to enclose and/or seal the cavity of the fluid containment structure. Cover layers of this embodiment may optionally be bound to the fluid containment structure so as to prevent leakage and facilitate handling of a fluid sample, for example using an adhesive layer positioned between the cover layer and the fluid containment structure, such as a laminating adhesive layer. Useful cover layers for sensors having an active fluidic delivery system have inlet holes and outlet holes for conducting the fluid sample through the sensor, optionally also including inlet and outlet flow connectors.

Fluid containment structures and photonic crystal structures of the present disclosure may comprise a wide range of materials including polymers such as mechanically flexible polymers. In embodiments useful for mass manufacture of disposable plastic sensors, the grating structures of the photonic crystal structure and the fluid containment structure are in the form of a monolithic, flexible polymer structure that is fabricated via molding or imprinting techniques. Use of a polymer material for integrated fluid containment and photonic crystal structures having a refractive index less than or equal to about n=1.6 is beneficial for some applications. In some embodiments, sensors of the present disclosure further comprise a supporting substrate, such as a polymer, glass, ceramic or composite substrate, provided to the sensor so as to support the fluid containment structure and the photonic crystal structure. Incorporation of a rigid substrate enhances the structural rigidity and flatness of the sensor to facilitate handling and optical readout of some sensors of the present disclosure.

Use of an at least partially optically transparent supporting substrate and/or rigid substrate is beneficial for some embodiments as this allows for optical read out by illuminating the bottom of the photonic crystal structure. In some embodiments, integrated fluid containment structures of the present disclosure are operationally connected to a mechanical support structure, such as a bottomless microplate frame, for example provided in a well microplate configuration, such as a standard 384 or 1536 microplate configuration to further increase the volume available for a sample.

In some embodiments, sensors of the present disclosure comprise a photonic crystal structure that is functionalized by incorporation of target material conjugated to an active surface of the photonic crystal such that the target material is exposed to the cavity of the fluid containment structure. In these embodiments, a target material may be provided having selective binding characteristics so as to provide selective detection and analysis of specific analytes present in a fluid sample. In these embodiments, binding of analyte to a target material conjugated to the active surface of the photonic crystal causes a change in refractive index in a probe region, thereby affecting the coupling of electromagnetic radiation into the photonic crystal and resulting in a change in photonic band gap. Useful target materials for biosensing applications include, but are not limited to, one or more: proteins, peptide, DNA molecules, RNA molecules, oligonucleotides, lipids, carbohydrates, polysaccharides; glycoproteins, lipoproteins, sugars, cells, bacteria, virus, candidate molecules and all derivatives, variants and complexes of these. As will be apparent to those skilled in the art, the target material may be conjugated to photonic crystal structures using a variety of techniques and linking systems know in the art of sensing and biosensing.

The present disclosure encompasses sensor arrays and sensing systems wherein a plurality of sensors is provided, wherein each sensor has individual integrated fluid containment and photonic crystal structures. In some embodiments, a plurality of fluid containment structures and photonic crystal structures are provided that comprise a single monolithic structure. In an embodiment, a plurality of sensors is provided that comprise sensing and active fluidic delivery components in a multichannel sensing systems. Alternatively, the present disclosure includes embodiments wherein a plurality of sensors is provided that make up sensing and fluid containment components in a multiwell array system. An advantage of the present sensors and related fabrication methods is that they may be provided in proximity to each other in a dense area format useful for lab-on-a-chip devices, multichannel sensing systems and microarray applications.

In another aspect, the present disclosure provides methods of making photonic crystal sensors having an integrated fluid containment structure. In one embodiment, a method of making a photonic crystal sensor having an integrated fluid containment structure comprises the steps of: (1) providing a master template having an external surface with a pattern comprising (a) a photonic crystal periodic surface grating structure and (b) structure for forming a fluid containment structure, the periodic surface grating structure located within the structure forming the fluid containment structure; (ii) transferring the pattern of the master template to a material such that the material forms a fluid containment structure having a cavity with the photonic crystal periodic surface grating structure positioned within the cavity; and (iii) depositing a thin dielectric film on the photonic crystal periodic surface grating structure to thereby forming a photonic crystal sensor. In an embodiment, the material is a polymer, such as a mechanically flexible, UV curable polymer. The fluid containment and photonic crystal structure are a monolithic structure (part of the same continuous polymer material) and are fabricated simultaneously. Deposition of thin dielectric films may be carried out by any means known in the art including chemical and physical thin film deposition techniques, such as magnetron sputtering, ion beam sputtering, plasma enhanced chemical thin film deposition, electron beam evaporation and thermal evaporation.

The manufacturing process may include replica molding process in which the transferring the pattern on the master grating basically forms a negative of the surface on the master template on the material. A periodic grating structure pattern having selected physical dimensions on the grating master is transferred to the material. Alternatively, the manufacturing method encompasses methods in which the pattern transfer is carried out using imprint lithography methods. Molding and imprinting fabrication methods of the present disclosure enable low cost, high throughput fabrication of photonic crystal arrays and sensing systems over very large areas (e.g., as large as 1 square foot at one time, upon a continuous roll of flexible substrate that may be thousands of meters in length). Methods of the present disclosure using replica molding for pattern transfer are beneficial because these methods do not require significant application of force to the external surface of the master template during pattern transfer, thereby avoiding damage to or distortion of grating structures in the master template relief pattern. This attribute of the present disclosure allows for repeat processing using a single master template and enhances pattern transfer fidelity. Use of polymer replica molding techniques are particularly beneficial as they can be carried out at room temperature and may be performed upon flexible and optically transparent substrates in a continuous roll-to-roll fashion.

Patterning of the master template to generate the periodic surface grating structure of the photonic crystal and the structures for forming fluid containment structures may be carried out by any means known in the art including deep UV optical lithography, E-beam writing, conventional optical lithography, optical write lithography, and micromachining. In some methods, the master template is generated by processing of a semiconductor wafer via a two step top down processing procedure, wherein nanosized grating structure features corresponding to a photonic crystal structure and a microsized a fluidic containment structures are defined in separate processing steps. In a first processing step, an external surface of the wafer is patterned with photoresist and etched so as to generate an external patterned layer having nanosized features provided in a spatially periodic configuration. This first processing step may be carried out, for example, using deep-UV lithography and reactive ion etching. In a second processing step, the external patterned layer of the semiconductor wafer is subsequently processed so as to define the structures that form the fluid containment structure. This secondary processing step may be carried out using conventional optical lithography and deep reactive ion etching.

BRIEF DESCRIPTION OF THE DRAWINGS

FIG. 2C is a schematic diagram illustrating the present method for making integrated fluid containment and photonic crystal structures using replica molding.

FIG. 3A is an illustration of a fabrication process used to produce a biosensor having microfluidic flow channel and photonic crystal positioned within the flow channel.

FIG. 5 is an illustration of peak wavelength value ("PWV") data gathered by the imaging instrument of FIG. 4 of a biosensor having three fluid channels incorporating a photonic crystal sensor, the three fluid channels filled with deionized (DI) water. FIG. 5D is a vertical cross-section plot showing PWV data along the vertical orange cross section line in FIG. 5a.

DETAILED DESCRIPTION

Biosensors are described herein which include one or more integrated fluid containment structures and a photonic crystal sensor, in a monolithic structure, e.g., a monolithic polymer structure. Fabrication methods for making biosensors and integral fluid containment structures will also be described below.

Figure 1A:
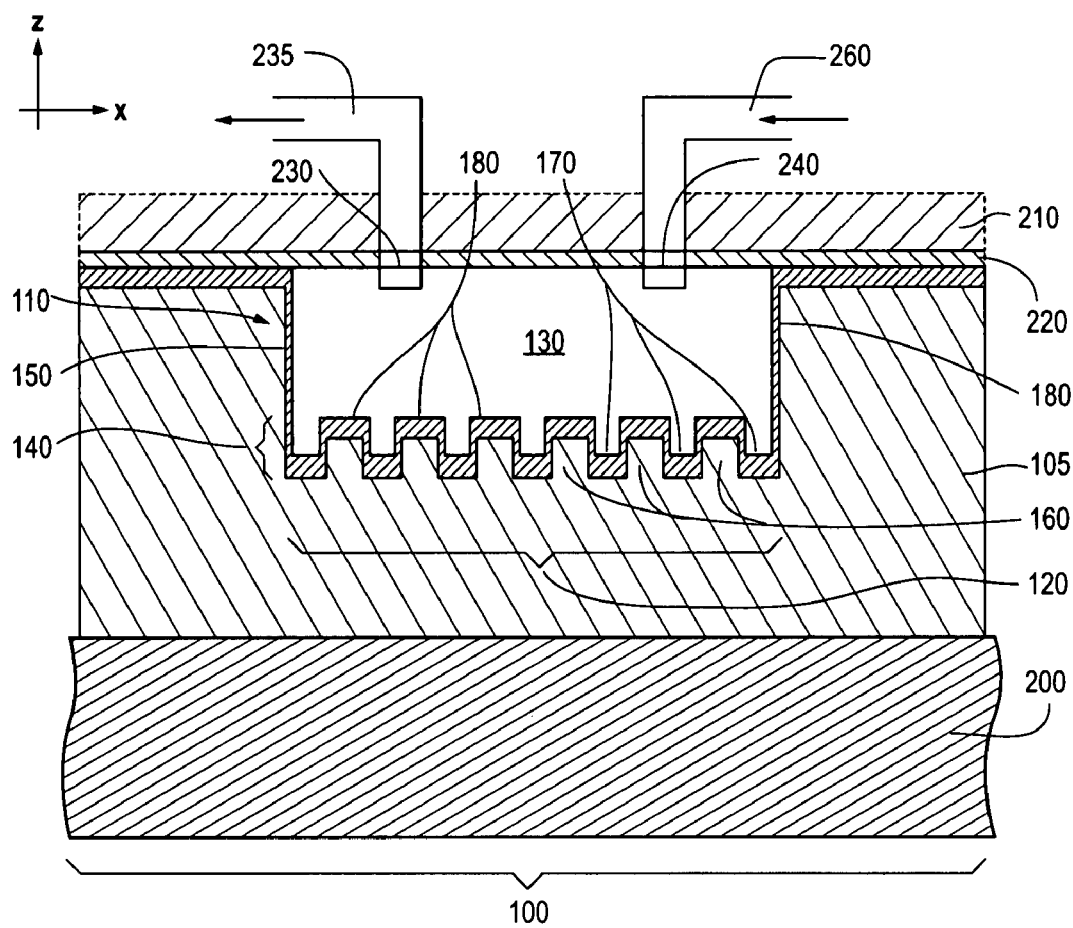
FIGS. 1A and 1B are schematic diagrams illustrating a cross section view (FIG. 1A) and a top plan view (1B) of a biosensor of the present disclosure having an integrated fluid containment structure and a photonic crystal sensor.

FIG. 1A is a schematic diagram illustrating a cross sectional side view of a biosensor 100 of the present disclosure having an integrated fluid containment structure 110 and photonic crystal sensor 120. FIG. 1A is not drawn to scale. The sensor shown in FIG. 1A can be considered as one unit cell and replicated in the X direction. The sensor extends into the page in the Y direction for some distance and the unit cell may repeat in the Y direction. The sensor is shown formed as a monolithic, layered structure. The base layer 200 is a substrate material, preferably and optically clear material such as polyethylene terepthalate (PET), and layer 105 is a clear polymer material such as UV curable epoxy.

The fluid containment structure 110 includes a cavity 130, which may take the form of a channel in a microfluidic system or a static reservoir such as a microwell in a micro array system. Cavity 130 has a bottom internal surface 140 and internal sides 150. Photonic crystal sensor 120 is provided on the bottom internal surface 140 of the cavity 130. As shown in FIG. 1A, the photonic crystal sensor 120 comprises a grating structure consisting of alternating high and low regions 160 and 170, respectively, provided in a one dimensional spatially periodic configuration, collectively forming a 1-D a linear grating structure. The grating structure 160/170 can be one dimensional (periodic in one dimension) or periodic in two dimensions, such as in the form of an array of posts or holes extending in the X and Y directions. Alternatively, the grating structure can take the form of 2-D, two-level grating.

A thin film 180 of a relatively high index of refraction material, such as a dielectric or semiconductor film, is provided on high and low structures 160 and 170. Optionally, thin films 180 are also provide on side surfaces of grating structures 160 and on side internal surfaces 150 of cavity 130 of the fluid containment structure 110. In a typical embodiment, the thin film 180 is a $TiO_2$ or $Ti_2O_3$ layer which is deposited onto the grating structure.

The grating structure 160/170 is formed in the material 105 in a manufacturing process to be described later on, such as for example a replica molding process using a grating master.

As shown in FIG. 1A, the grating structure 160/170 of the photonic crystal sensor 120 and the fluid containment structure 110 are constructed as a single monolithic structure, such as a monolithic polymer structure, in contrast to prior art in which a photonic crystal was manufactured separately and then fastened to another device such as a microwell plate. This monolithic structural configuration provides sensors having precisely aligned fluid containment structures and photonic crystal structures.

The substrate 200 can take the form of a polymer, ceramic or glass substrate, positioned to support the integrated fluid containment structure 110 and the photonic crystal structure 120.

Optionally, the sensor 100 further includes cover layer 210 positioned so as to enclose cavity 130 of the fluid containment structure 110. The cover layer 210 may be fastened to the fluid containment structure 110 by an adhesive layer 220, such as a laminating adhesive layer, and optionally may have an inlet 240 and inlet flow connector 260 and an outlet 230 and outlet flow connector 235 providing a means of flowing a fluid sample through the sensor 100. The arrows provided in FIG. 1A illustrate the flow of fluid sample through the sensor 100.

Figure 1B:
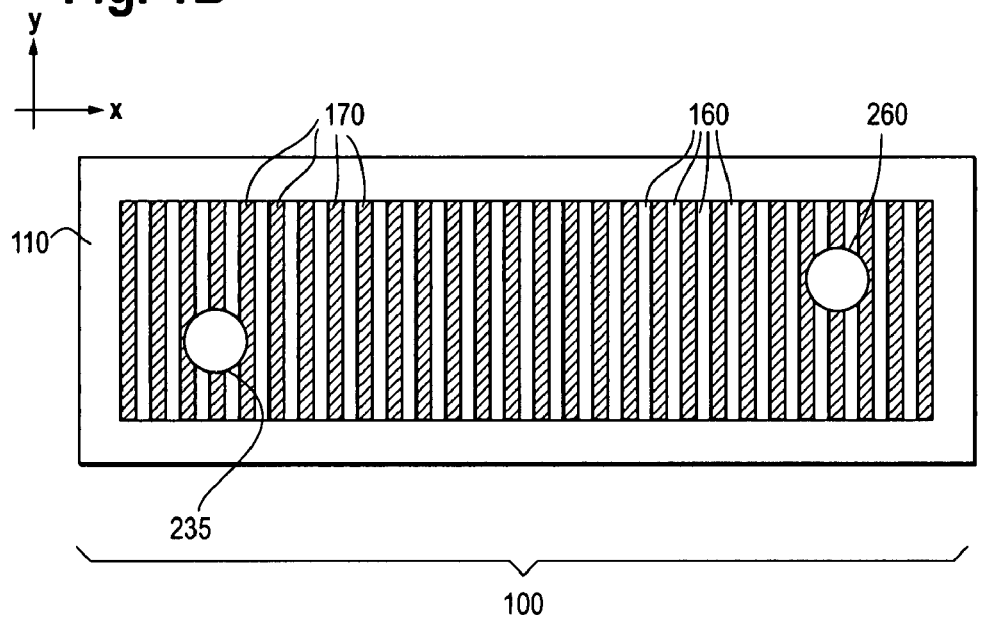

FIG. 1B shows a top plan view of the sensor 100 of FIG. 1A (not drawn to scale), with the cover layer 210 and adhesive layer 220 omitted. The fluid containment structure 110 is in the form of a microfluidic channel having a photonic crystal sensor on its internal bottom surface. For the sake of illustration, the thin films 180 on top surfaces of high and low grating structures 160 and 170 are omitted. Also shown in FIG. 1B are inlet flow connector 260 and outlet flow connector 235. The fluid containment structure 110 could also be considered to take the form of a vessel or well in which the sample to be tested is introduced into the well via the inlet connector 260 and removed via the outlet connector 235. In a variation, the fluid containment channel of FIG. 1B can extend in the Y direction and then change direction, e.g., be constructed to allow a fluid sample to flow along the fluid channel in a serpentine path (see FIG. 8 for example).

FIGS. 1C-1F are schematic diagrams illustrating several configurations for integrating a photonic crystal biosensor structure with an array of fluid containment cuvettes arranged in a standard 96-well microplate format, but manufactured as a single monolithic integrated structure. As with fluid channels intended for dynamic flow of fluid past and over the photonic crystal sensor surface, the cuvette fluid containment reservoirs are fabricated with a similar process that also produces at least one photonic crystal sensor on an internal surface of the cuvette fluid containment reservoir.

Figure 1C:
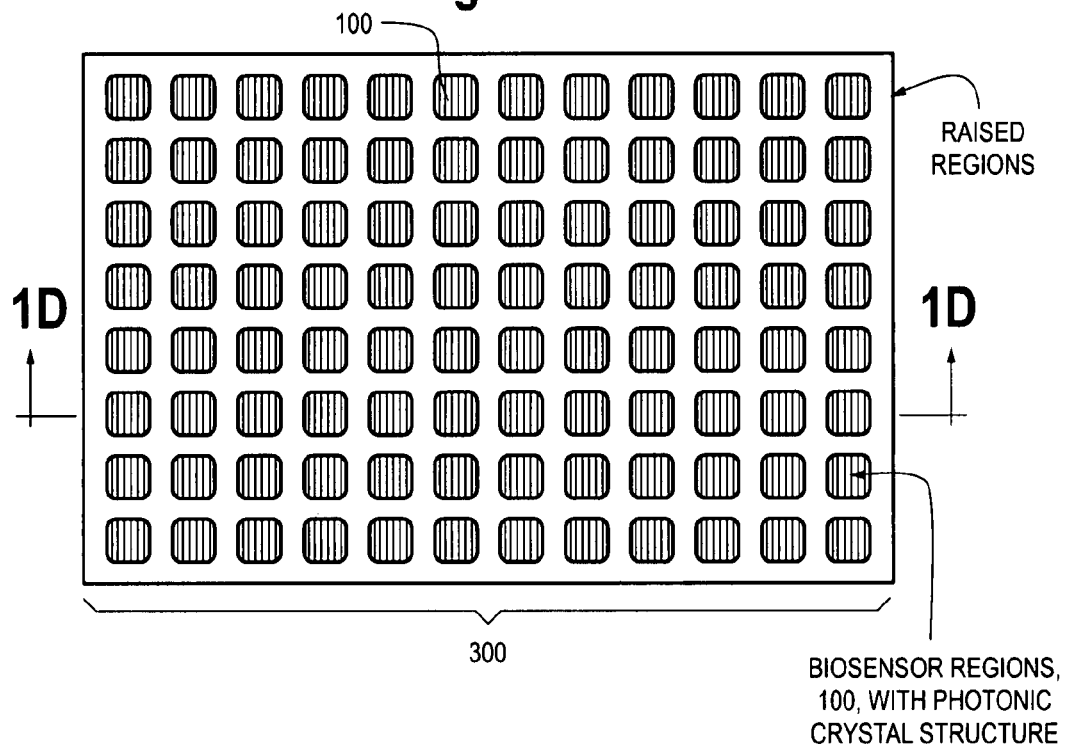
FIGS. 1C-1F are schematic diagrams illustrating several configurations for integrating a photonic crystal biosensor structure with arrays of fluid containment cuvettes arranged in a standard 96-well microplate format.
Figure 1D:
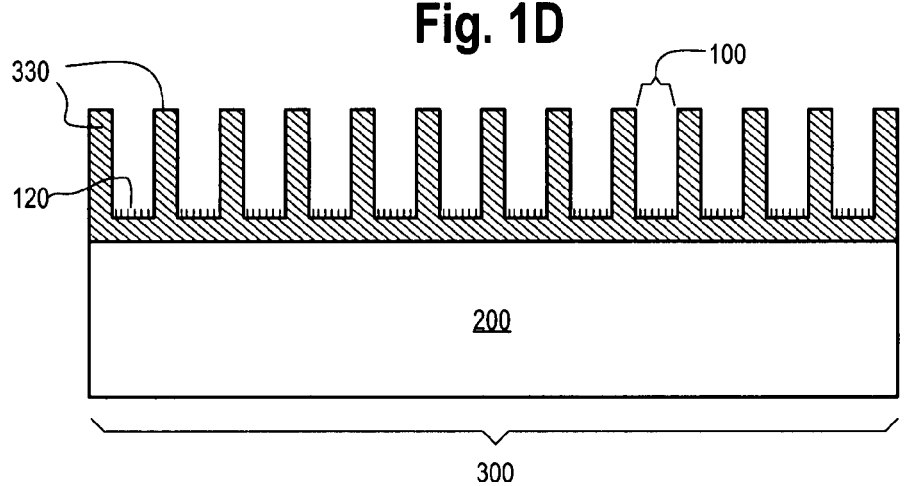

FIG. 1C shows a top view of a sensor array 300 comprising a plurality of biosensor cuvette sensors 100 each having integrated fluid containment and photonic crystal sensors. Each cuvette sensor 100 may have the general construction of FIGS. 1A and 1B. FIG. 1D shows a cross sectional view of the sensor array 300 showing the cured replica molded biosensor cuvette sensors 100 supported by an optically transparent plastic substrate 200. FIGS. 1C and 1D are not drawn to scale. As shown in FIG. 1D, each of biosensor cuvette sensors 100 comprises a fluid containment structure 330 (walls for holding a sample) and having a photonic crystal sensor 120 provided on its bottom internal surface. In some embodiments the fluid containment structures 330 have microsized physical dimensions (e.g., length, width and heights on the order of 10s or hundreds of microns), and the grating structures of photonic crystal sensors 340 having nanosized heights and width (on the order of 10s or 100s of nanometers), and micron-sized lengths in a one dimensional linear grating configuration.

Figure 1E:
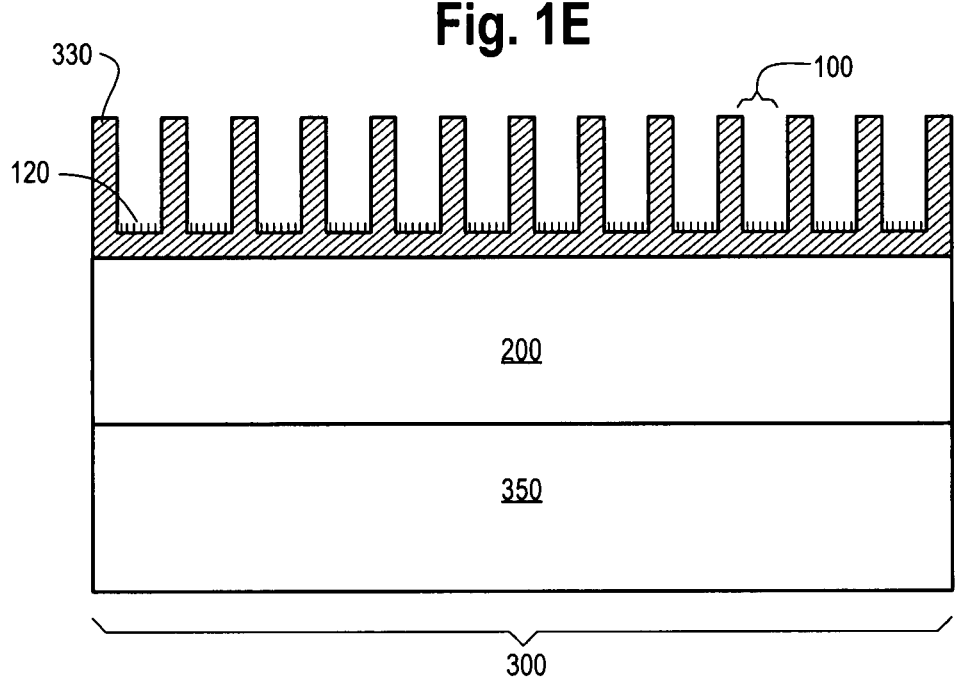

FIG. 1E is a cross sectional side view of an embodiment wherein a clear, rigid substrate 350 is further provided to support plastic substrate 200 of the sensor array 300 of FIG. 1C and 1D. The substrate 350 adds structural integrity and facilitates handling of the sensor array. Embodiments incorporating a rigid substrate 350 also maintain flatness of the photonic crystal structure, which is beneficial for ensuring reliable optical readout of the sensors.

Figure 1F:
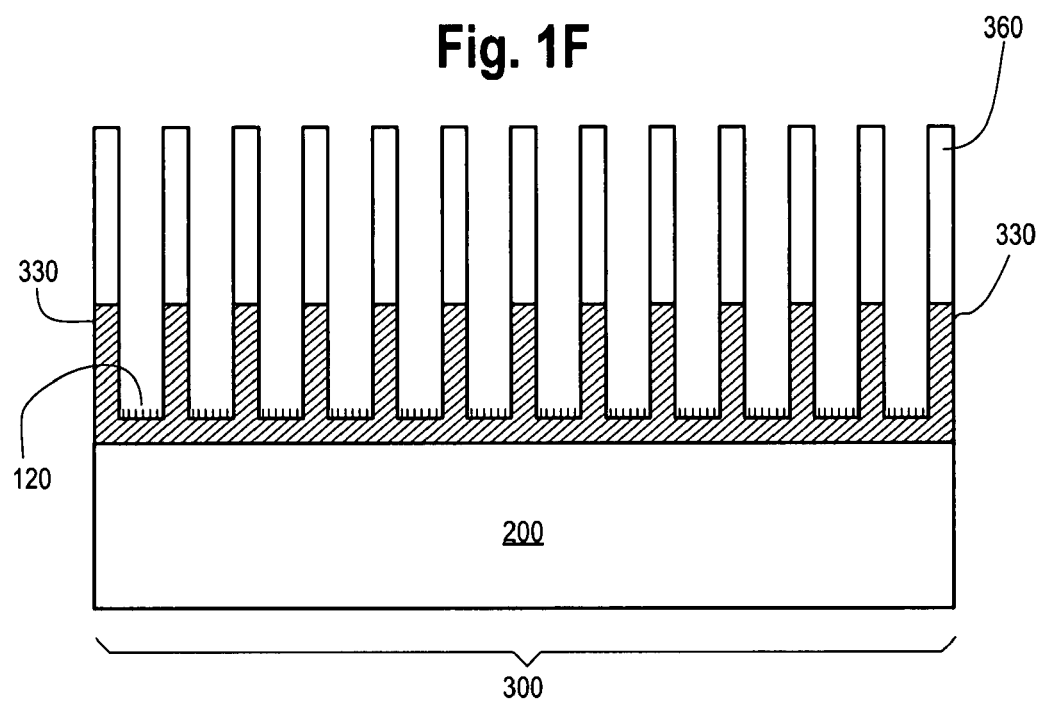

FIG. 1F is a cross sectional side view of an embodiment in which the fluid containment volume provided by the containment structures 330 is increased by incorporation of a bottomless microplate frame 360 to the upper surfaces of of the containment structures 330. The device configurations illustrated in FIGS. 1C-1F may be extended to sensor arrays having any number of reservoirs, including standard 384 and 1536-well microplate configurations.

Figure 2A:
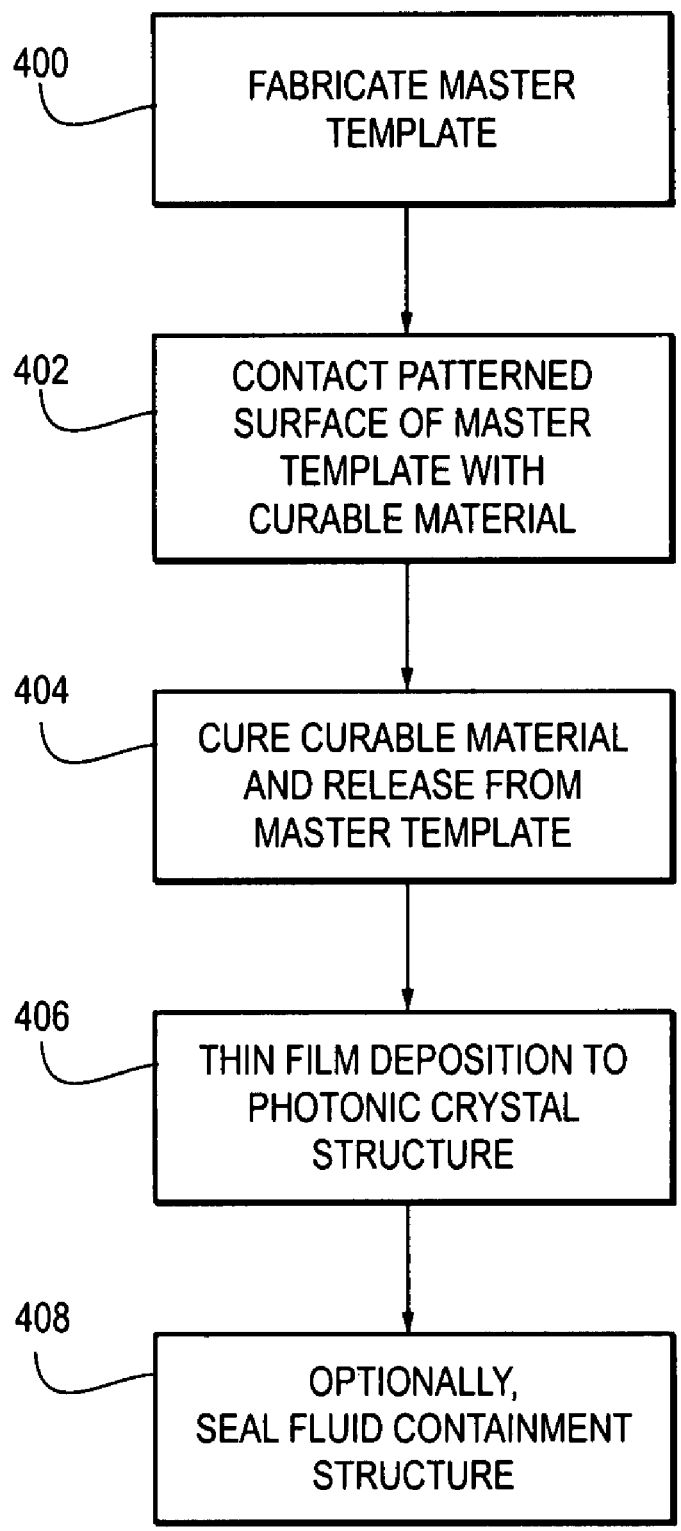
FIG. 2A is a process flow diagram illustrating an exemplary method for fabricating a sensor having an integrated fluid containment structure and a photonic crystal sensor.

FIG. 2A provides a process flow diagram illustrating an exemplary method for fabricating a biosensor in which the fluid containment and photonic crystal sensors structures are fabricated simultaneously, i.e., in the same manufacturing process. As shown in step 400 of this Figure, the first step is manufacture of a master template for use in a replica molding process. This step includes sub-steps of: (i) providing a silicon wafer; (ii) processing the external surface of the silicon wafer via deep-UV lithography to generate a periodic surface grating structure (e.g., a 1 or 2-D periodic grating). The periodic surface grating is used to form a photonic crystal having the surface grating structure 160/170 shown in FIG. 1 in the material 105. The step also includes sub-step (iii) of further processing the external surface of the wafer via conventional optical lithography to generate at least one micron-sized feature which forms the fluid containment structure, the fluid containment structure incorporating (surrounding) the photonic crystal grating structure.

In step 402, the patterned surface of master template form in step 400 is contacted with curable material. Step 402 includes sub-steps of: (i) providing the master template having the patterned external surface; (ii) contacting the patterned external surface of the master template with UV curable epoxy and (iii) allowing the UV curable epoxy to conform to the shape of features provided on the patterned external surface of the master template. The epoxy may be sandwiched between the patterned external surface of master template and a polymer (e.g., PET) substrate (substrate 200 in FIG. 1).

In Step 404 of FIG. 2A, the curable material is cured and released from the master template. This step includes sub-steps of (i) exposing the liquid UV curable epoxy in contact with patterned external surface of template to ultraviolet electromagnetic radiation to cure the UV curable epoxy, thereby generating a patterned polymer layer in contact with the master template; and (ii) peeling away the patterned UV material from the master template, thereby resulting in an integrated monolithic structure having a fluid containment structure and photonic crystal sensor.

In step 406 of FIG. 2A, thin films of high index of refraction material (180 and 190 of FIG. 1) are deposited on to the photonic crystal structure. For example, a layer of $TiO_2$ with a thickness of between 50-500 nm is deposited on the high and low surfaces of the periodic grating structure of the photonic crystal. The thin films may also be posited on the top surface of the fluid containment structure and the side walls as shown in FIG. 1A. The depositing of the thin dielectric film may, for example, be done by use of electron beam evaporation deposition or other suitable process.

In step 408 of FIG. 2A, the fluid containment structure is optionally sealed with of a cover layer, and optionally providing inlet and outlet ports in the cover layer. The cover layer can be adhered to the structure by means of an adhesive layer between the fluid containment structure and the cover layer. Inlet and outlet holes are then formed in the cover layer and the adhesive layer. Additional features such as tubes or ports or other similar structures can be added to facilitate attachment of vacuum, pump or injection devices to supply the sample to the sensor.

Figure 2B:
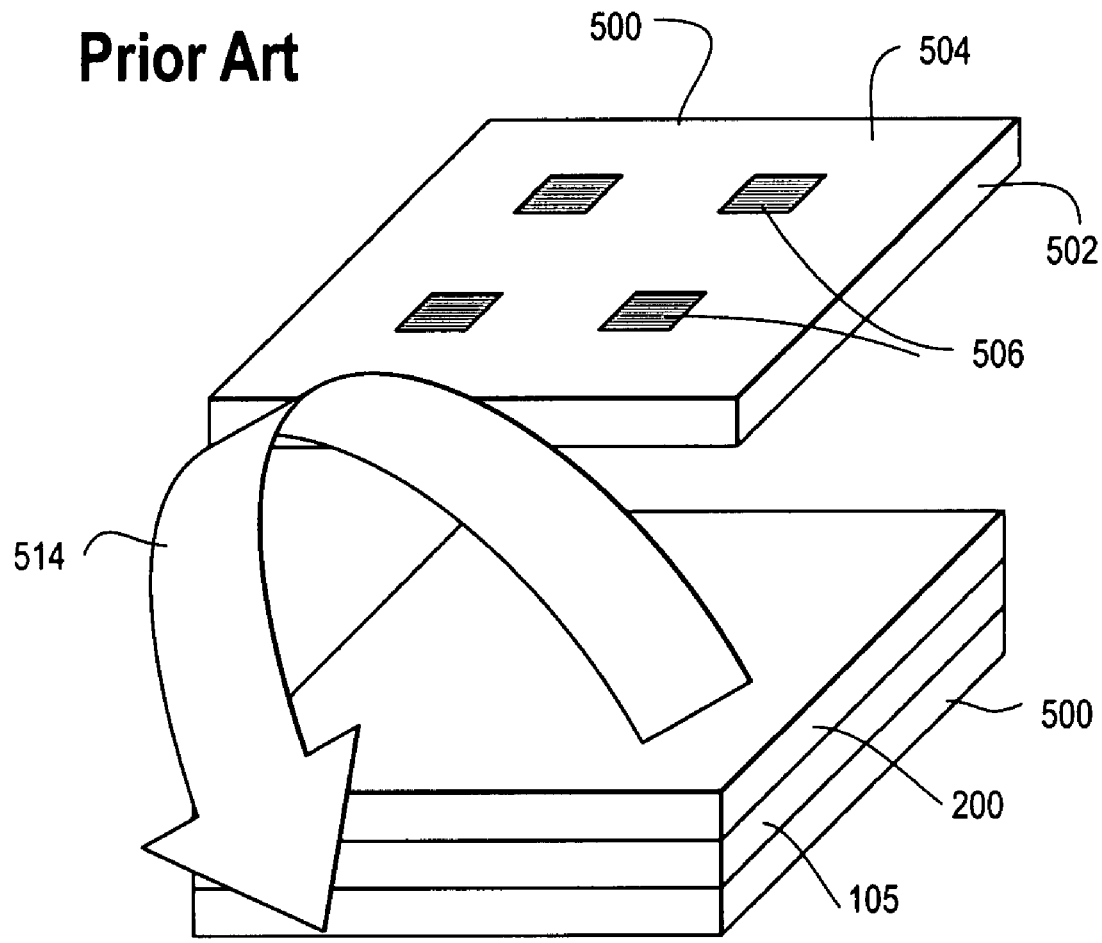
FIG. 2B is a schematic diagram illustrating a prior art method of making a photonic crystal sensor using replica molding.
Figure 2B:
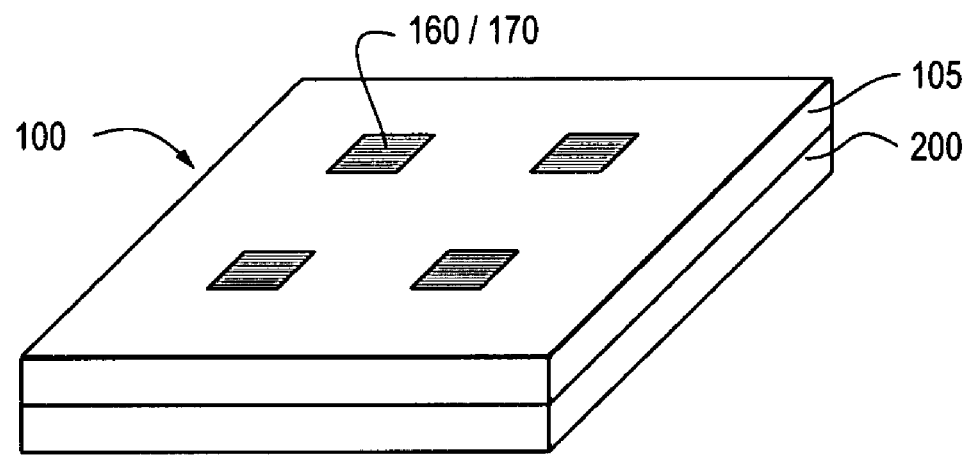

FIG. 2B provides a schematic diagram illustrating a prior art method of making a photonic crystal sensor using replica molding. As shown in this Figure, a silicon master template 500 is provided having silicon substrate 502 and an external surface 504 with a plurality of grating structures 506 corresponding to the grating structures of the photonic crystal sensors to be fabricated. In an embossing step, a layer of UV curable material 105 is applied to the external surface 504 of the template and allowed to conform to the shape of the grating structures in the master template 500. The layer of UV curable material 105 in contact with the external surface of the master template is also contacted with a PET backing layer 200. UV light is directed onto the material 105. The UV curable material 105 is cured and then removed from the silicon master 500. The resulting product is an array of photonic crystal structures.

FIG. 2C provides a schematic diagram illustrating the present method for making integrated fluid containment and photonic crystal structures using replica molding. As shown in FIG. 2C, the silicon master template is additionally patterned (etched) with structures 516 on its external surface corresponding to fluid containment structures, which in this example comprise a pair of fluidic channels 520. The structures 516 are low regions which become raised structures in a UV curable material whereas the regions 518 are high regions which become channels for allowing fluid to flow into and over the photonic crystal grating structure 506. As shown in the bottom panel of FIG. 2C, incorporation of the additional structures 516 results in simultaneous formation of the fluidic channels (fluid containment structures) and the photonic crystal structure upon the completion of the replica molding process. Furthermore, incorporation of the additional structures 516 provides for automatic and high precision alignment of the fluid containment channels 520 and the photonic crystal structures 506.

EXAMPLE 1

Single-step Fabrication and Characterization of Photonic Crystal Biosensors with Polymer Microfluidic Channels Introduction A method for simultaneously integrating label-free photonic crystal biosensor technology into microfluidic channels by a single step replica molding process is presented in this Example as one possible implementation of the disclosure.

By fabricating both the sub-micron features of the photonic crystal sensor structure and the >10 µm features of a flow channel network in one step at room temperature on a plastic substrate, the sensors are automatically self-aligned with the flow channels, and patterns of arbitrary shape may be produced. By measuring changes in the resonant peak reflected wavelength from the photonic crystal structure induced by changes in dielectric permittivity within an evanescent field region near its surface, detection of bulk refractive index changes in the fluid channel, or adsorption of biological material to the sensor surface is demonstrated. An imaging detection instrument is also described which characterizes the spatial distribution of the photonic crystal resonant wavelength, gathering thousands of independent sensor readings within a single fluid channel.

Recently, microfluidic lab-on-a-chip (LOC) devices and micro-total-analysis systems (µTAS) have been investigated in an effort to advance and simplify complex biochemical detection protocols for genomics, proteomics, pharmaceutical high-throughput compound screening, and clinical diagnostic/biomedical applications on a small chip. The need for an automated µTAS to measure large numbers of biochemical interactions is currently being driven by industries and biological research worldwide. To operate a microfluidic system and carry out large numbers of complex biochemical protocols, incorporation of sensors for feedback control and detection of biochemical interactions for process monitoring and verification is practically essential. This disclosure provides sensors which meet these requirements.

For the majority of assays currently performed, fluorescent or calorimetric chemical labels are commonly attached to the molecules under study so they may be readily visualized. However, using labels induces experimental uncertainties due to the effect of the label on molecular conformation, blocking of active binding epitopes, steric hindrance, inaccessibility of the labeling site, or the inability to find an appropriate label that functions equivalently for all molecules in an experiment. Therefore, the ability to perform highly sensitive biochemical detection without the use of fluorescent labels would further simplify assay protocols, and would provide quantitative kinetic data, while removing experimental artifacts from fluorescent quenching, shelf life and background fluorescence phenomena. While label-free biosensors have been incorporated within separately attached flow channels in the past, most systems are linked to a small number of independent sensor regions. What is needed is a sensor that enables highly parallel detection of biochemical interactions with a high area density of independent sensors that can function without crosstalk. Ideally, such a system could be easily integrated with a fluid flow network without the need to align the sensors with the flow channels. Ultimately, sensors distributed throughout a chip will be capable of monitoring hundreds of biochemical interactions, and providing real-time feedback to an integrated flow control system.

Previously, label-free optical biosensors based upon a sub-wavelength photonic crystal structure have been demonstrated. Because the photonic crystal structure does not allow lateral propagation of resonantly coupled light, a single photonic crystal surface is capable of supporting a large number of independent biosensor measurements without optical crosstalk between adjacent sensor regions. Using an image-based sensor readout method, we have demonstrated biosensor image pixel resolution as low as 9×9 $\mu m^2$, and have applied the imaging method to detect microarray spots, individual cells, and self-referenced assays within 96-well microplates. The photonic crystal surface has been produced over large surface areas from continuous sheets of plastic film, and has been incorporated into single-use disposable 96, 384, and 1536-well micro-plates (all of which can be imaged for biochemical binding density at 9×9 $\mu m^2$ pixel resolution over their entire surface area).

In this example, we present for the first time a novel technique for integrating label-free photonic crystal biosensor technology into microfluidic networks by replica molding photonic crystal sensors and fluid channels simultaneously. This approach enables detection modalities such as label-free biochemical detection, sample bulk refractive index detection, and fluid presence within microchannels. By fabricating multiple parallel channels in close proximity, high throughput biochemical assays are enabled. Accurate correction of common-mode error sources such as temperature and bulk solution refractive index variability is enabled by using sensors embedded in one of the parallel channels as a reference.

The single step integration of photonic crystal biosensor structures into microfluidic channels presented here is also performed upon flexible plastic substrates using a replica molding approach to enable a simple low-cost manufacturing process to produce sensors and flow channels of arbitrary shape that are automatically aligned to each other. Disposable plastic chips would be less expensive than reusable glass devices and would eliminate time-consuming regeneration steps. In addition, the polymer used for the molded structure has superior solvent resistance and gas permeability properties as compared to polydimethylsiloxane (PDMS), where incompatibility with most organic solvents has limited its use to aqueous-based applications. Finally, through the use of an image-based detection approach, this system is capable of observing the spatial profile of biochemical binding within the fluid channel, both across the channel width, and along the channel length.

Materials and Methods

1. Microfluidic Sensor Fabrication

The fabrication process requires a method that can accurately produce sub-micron features for the photonic crystal structure, while at the same time producing the >10 µm features of the microfluidic channel. A replica-molding process using a rigid "master" structure and a UV-curable liquid polymer material was selected for this purpose because the molding may be performed at room temperature without the requirement to exert a large force between the mold and the molded material.

An outline of the fabrication procedure is shown in FIG. 3a. First, a silicon master wafer 500 with 550 nm period 1-D linear grating structures 506 was fabricated. The grating structures 506 were patterned with photoresist using deep-UV lithography, in which 6.7 mm diameter circular dies were stepped and repeated every 9 mm. After the exposed photoresist was developed, the patterned grating structure was transferred to the silicon wafer by reactive ion etch to a depth of approximately 170 nm. After etching, the photoresist was removed. Next, the fluid channel structures 516 were patterned onto the same silicon master wafer with grating structures from the previous step using photoresist again, but with conventional lithography. Because high resolution is not required for defining the channels (channel widths of 30-250 μm were investigated), and to maximize flexibility for investigating different channel shapes, the photomask for the channel patterns was produced upon a transparent plastic sheet with 5080 dpi high resolution printing. After developing the exposed photoresist, channel structures 516 were transferred onto the silicon wafer using deep reactive ion etch with depth of approximately 20 μm, followed by removal of photoresist. As a result, a negative pattern template of microfluidic channels incorporated with sub-micron scale linear grating structures was formed. Subsequently, the completed silicon template was treated with repel silane (GE Healthcare) to promote clean release of replica from the template without contaminating the template structures with polymer residues.

Figure 3B:
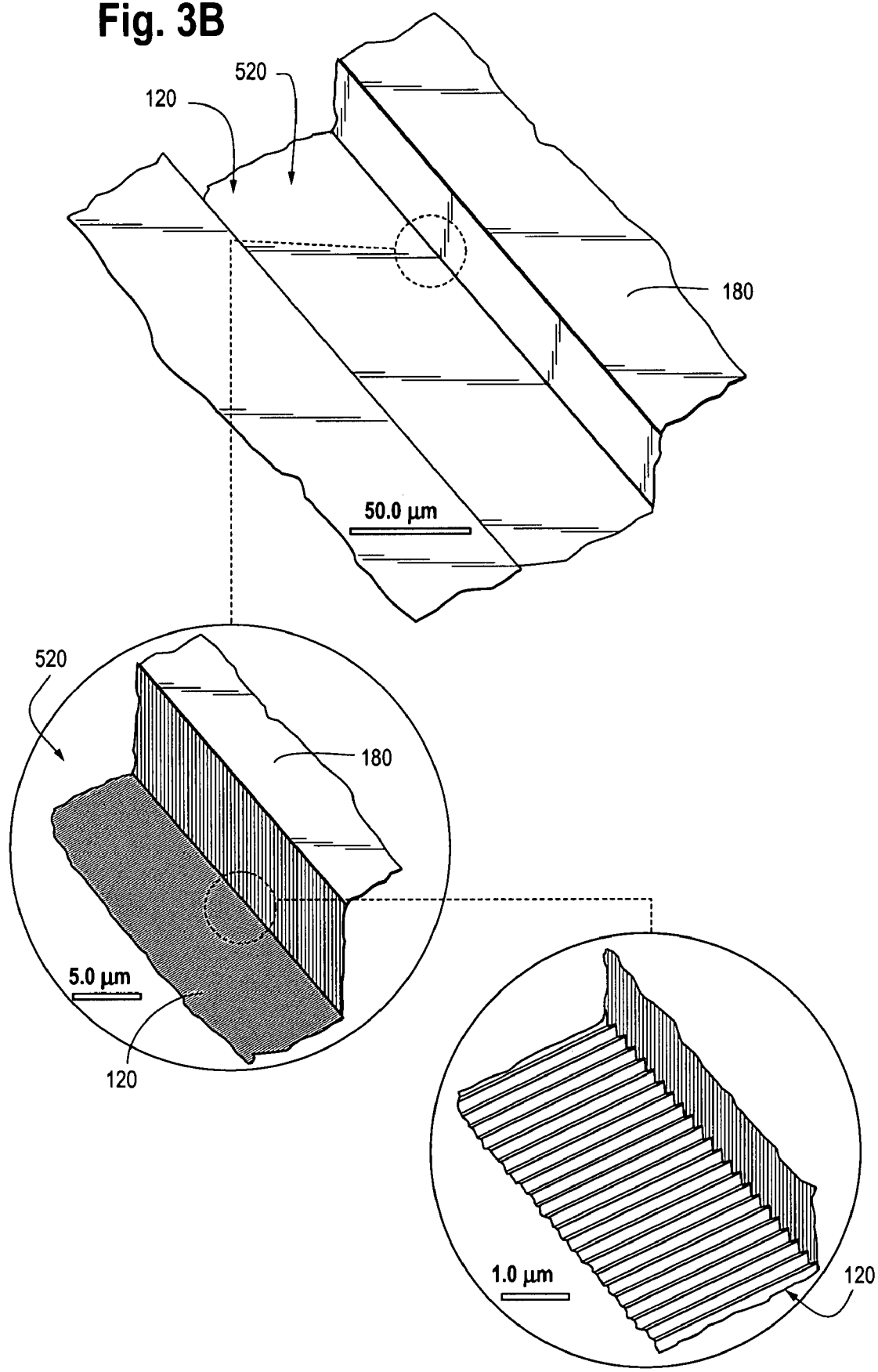
FIG. 3B is a scanning electron micrograph of microfluidic channels with embedded photonic crystal sensors.

Utilizing the silicon master wafer as a mold, the surface structure 506/516 of the master wafer 500 was replicated onto a 250 μm thick flexible polyethylene terephthalate (PET) substrate 200 by distributing a layer of liquid UV curable polymer 105 between the silicon master wafer 500 and the PET substrate 200. The liquid polymer conforms to the shape of the features on the master wafer, and is subsequently cured to a solid state by exposure to UV light 600. After the polymer was cured, the surface structure was peeled away from the silicon wafer, leaving behind a replica of the silicon master wafer surface adhered to the PET sheet (FIG. 3 (iv)). The sensor was completed by depositing approximately 150 nm of titanium dioxide ($TiO_2$) shown as layer 180 in FIG. 3 (v) using electron beam evaporation on the replica surface. The Scanning Electron Micrograph (SEM) images in FIG. 3*b* show the cured replica surface coated with $TiO_2$, in which the replicated flow channel 520 contains the photonic crystal biosensor 120 on its bottom surface.

The upper surface of the microfluidic channel 520 was completed by sealing with a separate PET sheet 210 with inlet and outlet holes, using a layer of 2-sided pressure-sensitive adhesive film 220 (3M) in between (FIG. 3, part (vi)). The sealed plastic microfluidic sensor chip was then attached with the same transparent film adhesive to the surface of a 1×3 square inch glass microscope slide to provide structural rigidity. The microfluidic sensor chip was completed by attaching polypropylene (PP) flow connectors on the inlet holes of the PET cover layer using adhesive, followed by reinforcement sealing with clear epoxy. Flowing fluids into the microfluidic channels 520 was accomplished by pre-filling the PP flow connectors with solutions or analytes and manually pumping it using a syringe with tubing connected to PP flow connector. Manual syringe pumping method was sufficient because experiments performed in this work involved filling the channels with solutions, incubating/stabilizing at room temperature, washing/rinsing with buffer, and therefore were independent of fluid flow rate.

2. Imaging Instruments

As will be recognized by those skilled in the art, a great variety of optical illumination, analysis and detection systems may be used in conjunction with the present sensors, for example as described in the previously-cited patent literature. Such instruments will typically include suitable illumination apparatus, and optical and detection components so as to enable optical read out, including read out in optical imaging and point detection modes. The instruments include a light source positioned in optical communication with the sensor such that the photonic crystal structure is illuminated with electromagnetic radiation having a selected wavelength distribution, for example electromagnetic radiation having a wavelength distribution in the visible, ultraviolet or infrared regions of the electromagnetic spectrum. A photodetector is positioned in optical communication with the photonic crystal structure such that it is capable of analyzing and detecting electromagnetic radiation reflected, scattered or transmitted by the photonic crystal structure. Useful optical sources include broad band sources, including quartz lamps, xenon lamps, halogen lamps and/or deuterium lamps. Useful photodetectors comprise optical analyzers including dispersive elements, such as spectrometers, gratings and prisms, and optical detectors such as photomultipler tubes, photodiodes, diode arrays and CCD imaging systems.

In one possible embodiment, the optical source is a broad band source in combination with a polarization filter that provides electromagnetic radiation at normal incidence to the sensor having a polarization direction perpendicular to grating lines of the photonic crystal structure. A beam splitter and imaging lens is provided to collect electromagnetic radiation reflected from the sensor and direct it to the aperture of a spectrometer. Detection is carried out using a two dimensional detector, such as a CCD camera. In this optical read out configuration, electromagnetic radiation from a line on the photonic crystal structure is wavelength analyzed and detected, optionally as a function of time. Spectral analysis provided by this detection configuration provides a spatially resolved spectrum for each point within the line, thereby allowing determination of the wavelength distribution, and optionally peak wavelength for each point on the line. The detection system may further include a motorized stage capable of translating the sensor such that two dimensional images of the photonic crystal structure are obtained. Alternatively, the detection instrument may include optical instrumentation capable of scanning the illuminating beam of electromagnetic radiation over selected regions of the sensor such that two dimensional images of the photonic crystal structure are obtained.

Figure 4:
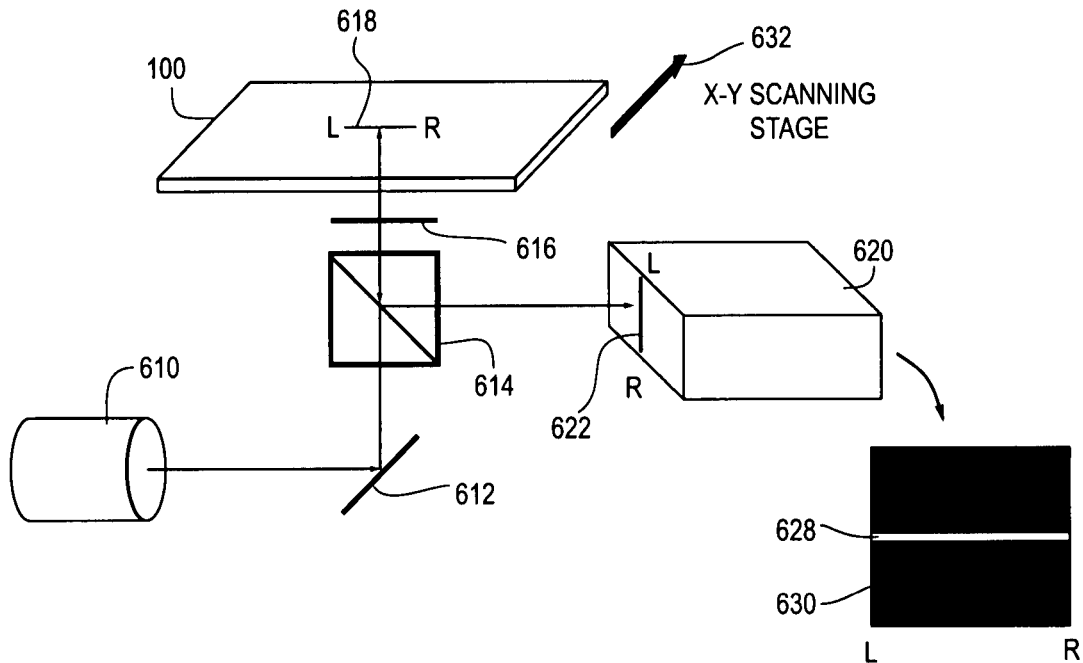
FIG. 4 is a schematic diagram of a representative imaging readout instrument for use with the biosensors of this disclosure.

A schematic diagram of a biosensor peak wavelength value (PWV) imaging instrument used in Example 1 is shown in FIG. 4. The instrument includes a light source 610, mirror 612, beam splitter 614, a polarizing filter 616 and an imaging spectrometer 620. White light from the light source 510 illuminates the sensor 100 at normal incidence, with a polarization filter 616 to only allow passage of light with polarization direction perpendicular to the sensor grating lines. The reflected light is directed through the beam splitter 614 to an imaging lens of unity magnification (not shown) and to a narrow entrance slit aperture 622 of an imaging spectrometer 620. The width of the slit 622 may be set at a desired value, e.g. within a range from 6 to 200 82 m. Using this method, reflected light is collected from a line on the sensor 100 surface, where the width of the imaged line is determined by the width of the entrance slit 622 of the imaging spectrometer. The imaging spectrometer 620 contains a two-dimensional CCD camera (Acton Research) with 2048×512 pixels. The line of reflected light, containing the biosensor resonance signal, is diffracted by a diffraction grating in the spectrometer 620 to produce a spatially-resolved spectrum from each point within the line. When the CCD camera is operated in 2048×512 pixel mode, the line-image through the slit is imaged onto 512 pixels. A spectrum, with a resolution of 2048 wavelength data points, is acquired for each of the 512 pixels. Upon peak-finding analysis of all 512 spectra, the PWVs of 512 pixels are determined. Thus, a line 628 of 512 pixels is generated for the PWV image 630 of the sensor.

To generate a two-dimensional PWV image of the sensor, a motorized stage (not shown) translates the sensor 100 which is placed on a precise holding fixture, in the direction that is perpendicular to the image line. See arrow 632 in FIG. 4. The spatial separation of the image lines is determined by the step-size of the stage between each image-line acquisition (In addition, the CCD can be read out with various resolutions by binning pixels). By this technique, a series of lines are assembled into an image through software and same spot in the sensor can be scanned repeatedly after the sensor has been translated. In the current system, the length of the image line is 9.1 mm, as determined by the size of the CCD chip, across the biosensor surface. A large area can be scanned in a tiled fashion, where the width of a tile is 9.1 mm, by translating the sensor in steps of 9.1 mm along the image-line direction.

Typically, a biosensor experiment involves measuring shifts in PWV, so the sensor surface is scanned twice, once before and once after biomolecular binding, and the images are aligned and subtracted to determine the difference in PWV as detected by the sensor. This scanning method does not require the PWV of the imaged surface to be completely uniform, either across the surface or within a set of probe locations, or tuning of the sensor angle to a resonance condition as with Surface Plasmon Resonance (SPR) imaging.

Results and Discussion

1. Bulk Refractive Index Sensitivity Experiment

The sensor structure integrated within the fluid channels measures changes in dielectric permittivity upon its surface. Therefore, flowing liquid solutions with variable refractive index through the fluid channels induces a PWV shift. Because refractive index corresponds linearly with dimethyl sulfoxide (DMSO) concentration in deionized (DI) water, the dependence of PWV on bulk refractive index was determined by flowing in different concentrations of DMSO solution in DI water to the fluid channels.

In this experiment, a sensor 100 having three fluid channels, each having its own photonic crystal sensor in the bottom thereof, was used. The three channels are designated p1, p2 and p3 in the following discussion and in FIGS. 5 and 6.

Figure 5A:
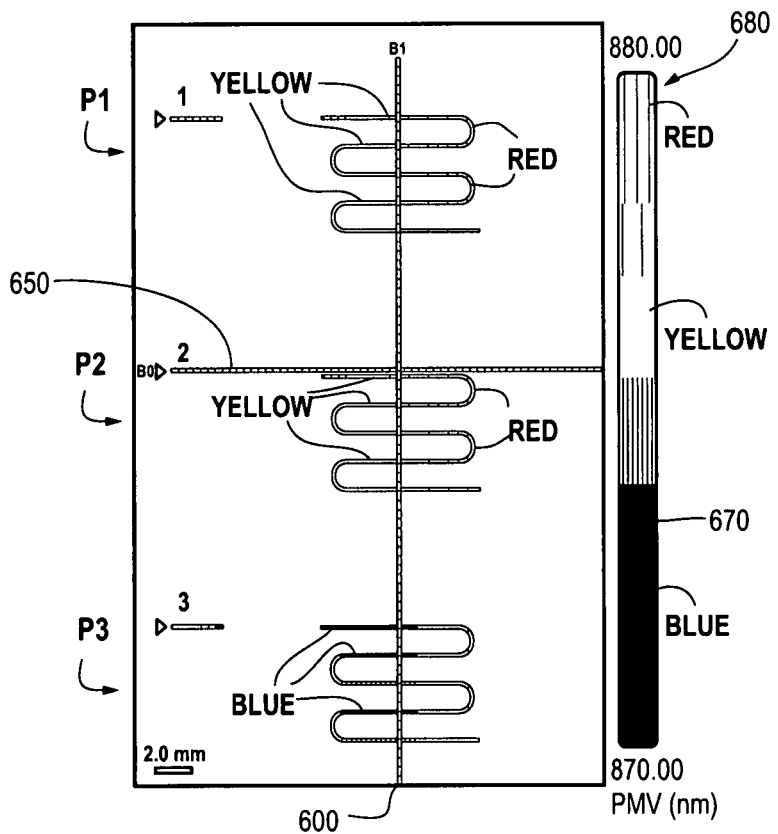
FIG. 5A shows the spatial PWV image of the three channels. PWV shifts are represented by the scale bar ranging from 870 nm to 880 nm.
Figure 5B:
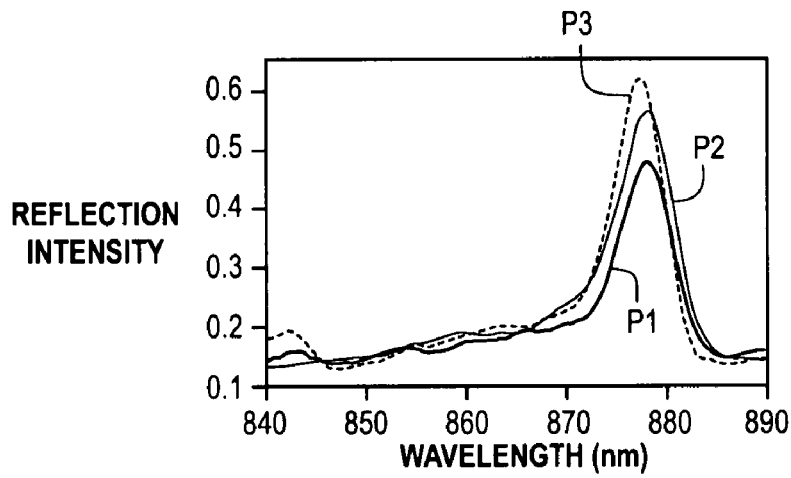
FIG. 5B are graphs of sample reflection spectra from each of the three channels.
Figure 5C:
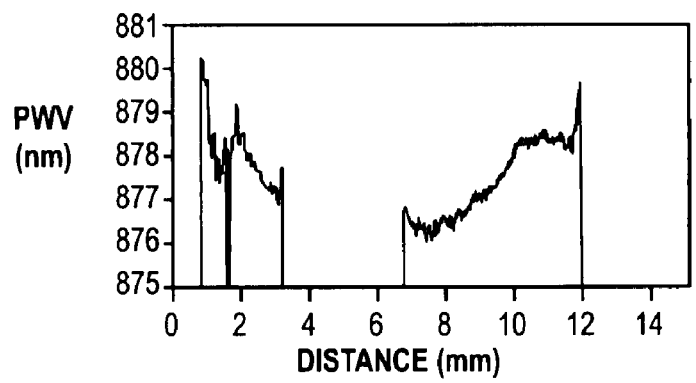
FIG. 5C is a horizontal cross-section plot showing PWV data along the green horizontal cross section line in FIG. 5A.
Figure 5D:
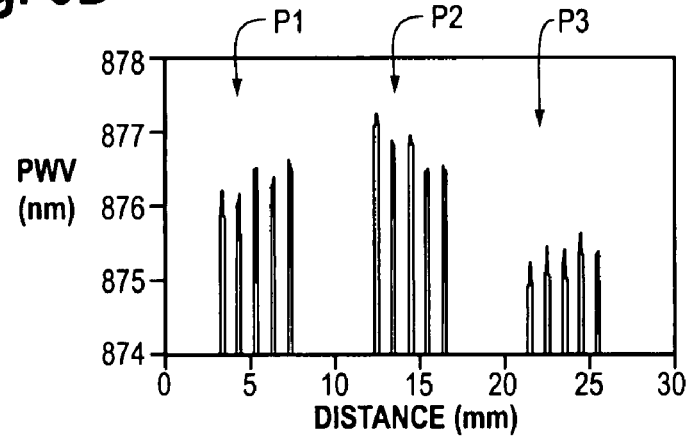

Initially, all three channels were filled with DI water and a baseline PWV imaging scan at 22.3 µm resolution was made using the instrument. The resulting spatial PWV image is shown in FIG. 5a, in which PWVs are represented by the scale bar 670 ranging from 870 nm to 880 nm, with red region 680 representing areas of higher PWV. FIG. 5b shows sample reflection spectra from one data pixel from each channels, with PWVs of 877.79, 877.65, 876.87 nm for channels p1, p2 and p3, respectively. FIGS. 5c and 5d are cross section plots of the spatial PWV image. The plot in FIG. 5c represents PWVs along the green horizontal cross section line 650 of FIG. 5a, and likewise, FIG. 5d represents PWVs along the orange vertical cross section line 660 of FIG. 5a. The cross section PWV plots indicate that the PWVs vary slightly from different channels and even within the same channel (FIG. 5c). This is acceptable since quantity of interest in this case is the shift in PWV when different solutions are introduced or some biochemical reaction occurs on the sensor surface, rather than the PWV value itself.

Figure 6A:
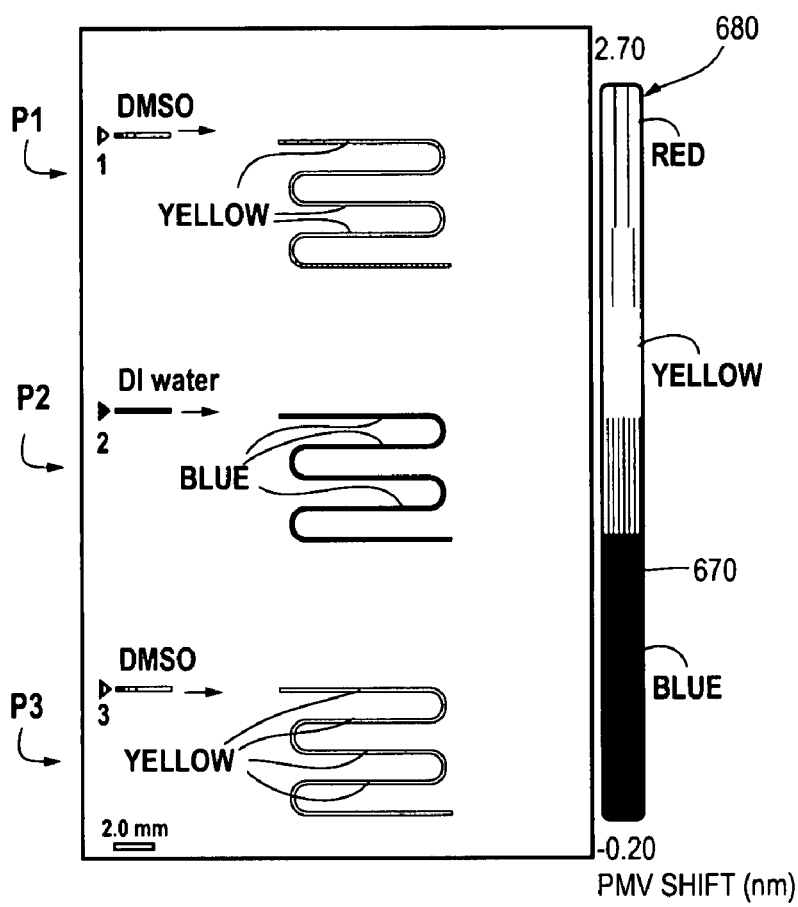
FIG. 6A is an illustration of the PWV shift measured by flowing in 6.25% dimethyl sulfoxide (DMSO) solution through channels 1 and 3, and flowing in DI water through channel 2 to serve as reference. PWV shifts are represented by the scale bar from −0.20 to 2.70 nm, where the red region represent areas of greater positive shift.

After taking a PWV image scan with the channels filled with DI water, channels 1 and 3 were filled with DMSO solution while channel 2 was refilled with DI water, to serve as a reference. FIG. 6a shows a spatial PWV shift image measured by flowing in 6.2S % DMSO solution through channels 1 and 3. Shifted PWV image is obtained by subtracting the reference spatial PWV image with all channels filled with DI water (FIG. 5a), from the spatial PWV image of the exact same device filled with 6.2% DMSO solutions in channels 1 and 3.

Therefore, PWV variations caused by fabrication non-uniformity shown in FIGS. 5a, c, and d does not result in significant sensitivity non-uniformity as PWV image subtraction is performed. PWV shifts are represented by the scale bar 670 from −0.2 to 2.7 nm, where red regions represent areas of greatest positive shift. The overall standard deviation for shifted PWV of data was 0.263 nm.

Once the shifted PWV images are obtained, grids of sensor regions are selected (Square areas in FIG. 6a), in which many independent pixel readings within each grid can be averaged into a single measurement. A masking function is applied so that only resonant peaks with reflected intensity maxima above a user-selectable value are considered for the selection of spectra within the grid. Through the masking function, therefore, regions of the chip that do not contain a photonic crystal structure (such as the regions between flow channels) that do not reflect a resonant peak, are automatically eliminated from further consideration. Each grid can be designated as "active" or "reference", and PWV shifts from reference regions can be associated with any desired active region for subtraction of common-mode artifacts. In this experiment, the PWV shift was calculated by subtracting the average PWV shift within the grid of channel 2 (reference), from the average PWV shift of the grids for channels 1 and 3 (active). Because of the differences in channel width (150, 200, and 250 µm for channels 1, 2, and 3 respectively), the number of independent data pixels satisfying the mask function within each grid for channels 1, 2, and 3 were 2560, 4337, and 7509 respectively.

Figure 6B:
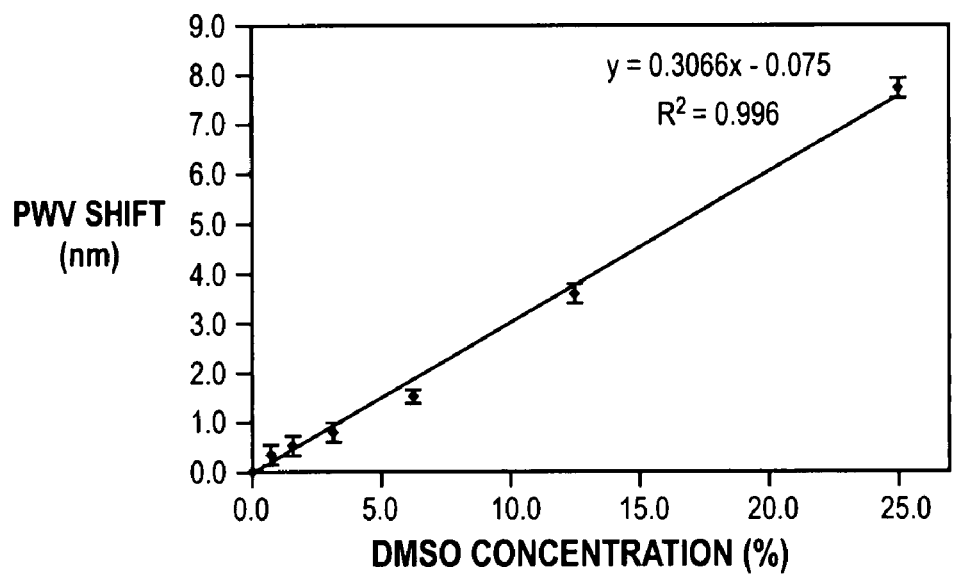
FIG. 6B is a plot of PWV shift measured with DMSO solution with concentration ranging from 0% to 25%, in which the data points were linearly fitted with least square approximation with $R^2$ value equal to 0.996.

Scans were made after flowing in each of the different DMSO concentrations ranging from 0.78% to 25% through channels 1 and 3. Both channels were rinsed with DI water and dried before flowing in different concentrations of DMSO solutions. FIG. 6b plots the PWV shift as a function of DMSO concentration, in which the data points were linearly fitted with least square approximation with $R^2$ value equal to 0.996, showing the expected linear dependence between photonic crystal reflected resonant PWV and the solution bulk refractive index. The approximate bulk refractive index change corresponding to 6.25% change in DMSO concentration ($\Delta$ PWV of 1.841 nm) is 0.00682, based on the bulk refractive index shift coefficient ($\sigma=\Delta PWV/\Delta n$) value of 270, determined from previous research.

2. Protein A—Immunoglobulin G (IgG) experiment

An experiment was performed to demonstrate detection of biomolecular binding on the surface of the photonic crystal sensor within the fluid channels. Protein A (Pierce Biotechnology) was used as the immobilized protein ligand on the sensor surface, while chicken IgG and pig IgG (Sigma-Aldrich) were used as analytes. Pig IgG is known to have a strong binding affinity for Protein A, while chicken IgG is known not to bind with Protein A, and therefore acts as a negative control for our experiment.

Figure 7A:
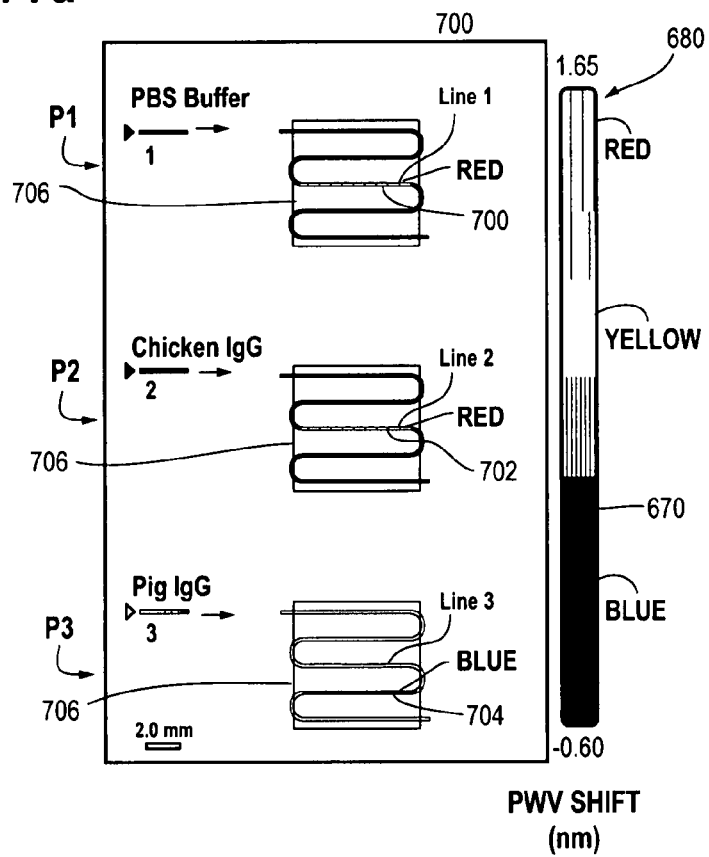
FIG. 7a is a shifted PWV image (subtraction of the PWV image of protein A coated channels from PWV image with channels 2 and 3 bound with IgG molecules). The amount of shifts are represented by the scale bar from −0.60 to 1.65 nm, where red regions represent areas of greatest positive shift.

Before immobilization of Protein A, a baseline PWV image of three channels filled with PBS buffer (Sigma-Aldrich) was taken at a pixel resolution of 22.3 µm. The Protein A was attached by simple physical adsorption by flowing a 0.5 mg/mL solution through all three channels p1. p2 and p3, allowing the solution to incubate for 10 minutes, followed by washing away of unbound Protein A with PBS buffer. A second PWV image was gathered after Protein A immobilization, with PBS buffer in the channels. Next, channel 1 was filled with PBS buffer to serve as a reference, while channels 2 and 3 were filled with 0.5 mg/mL concentration solutions of chicken IgG and pig IgG respectively. The IgGs were allowed to incubate with the immobilized Protein A for 10 minutes, followed by a thorough PBS wash to remove unbound IgGs. Then, a final PWV scan was made with all three of the channels filled with PBS buffer FIG. 7a shows a PWV shift image for subtraction of the PWV image after Protein A coating from the PWV image after IgG binding for all three channels. PWV shifts are represented by the scale bar 670 from −0.60 to 1.65 nm, where red regions 680 represent areas of greatest positive shift. As shown in FIG. 7a, three horizontal lines 700, 702 and 704 within each channels (lines 1, 2 and 3 colored in orange, red and blue respectively) are selected, in which independent PWV shift pixel data along the lines are sampled. The number of independent data pixels sampled within each line is 190.

Figure 7B:
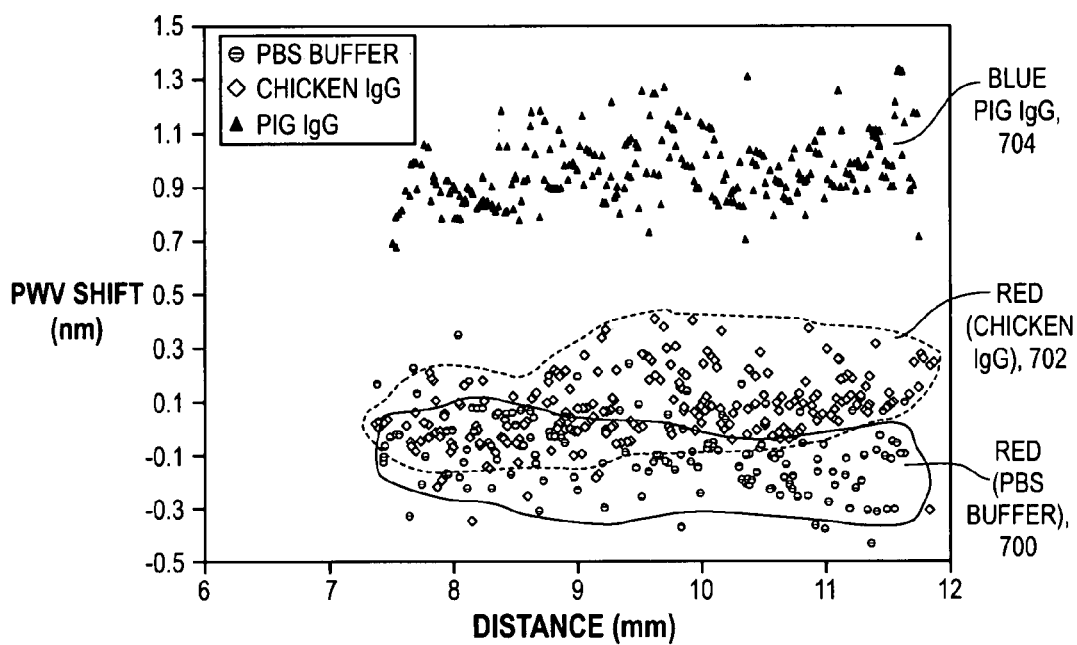
FIG. 7b is a cross-sectional PWV shift plot along lines 1, 2 and 3 for each of the three channels for PBS buffer, chicken IgG, and pig IgG respectively.

FIG. 7b is the cross sectional PWV shift plot along lines 1, 2 and 3 (700, 702, 704) for each of the three channels for PBS buffer, chicken IgG, and pig IgG, respectively. In order to calculate the overall PWV shifts for the IgGs, square grids 706 of sensor regions, shown in FIG. 7a, are selected, in which many independent pixel PWV data within each grid 706 can be averaged. Again, because of the differences in channel width (150, 200, and 250 µm for channels 1, 2, and 3 respectively), the number of independent data pixels sampled within each grid for channels 1, 2, and 3 were 2223, 5449, and 6208, respectively. For this experiment, the overall average PVVV shifts for IgGs were calculated by subtracting average PWV shift within the grid of channel I which is the reference, from average PWV shift of grids for channels 2 and 3 corresponding to chicken IgG and pig IgG, respectively. Using the above method, the average PWV shift measured and calculated in the chicken IgG and pig IgG containing sensor channels were −0.051 and 0.815 nm, respectively, demonstrating selective attachment of the Pig IgG analyte to the immobilized Protein A.

Figure 8:
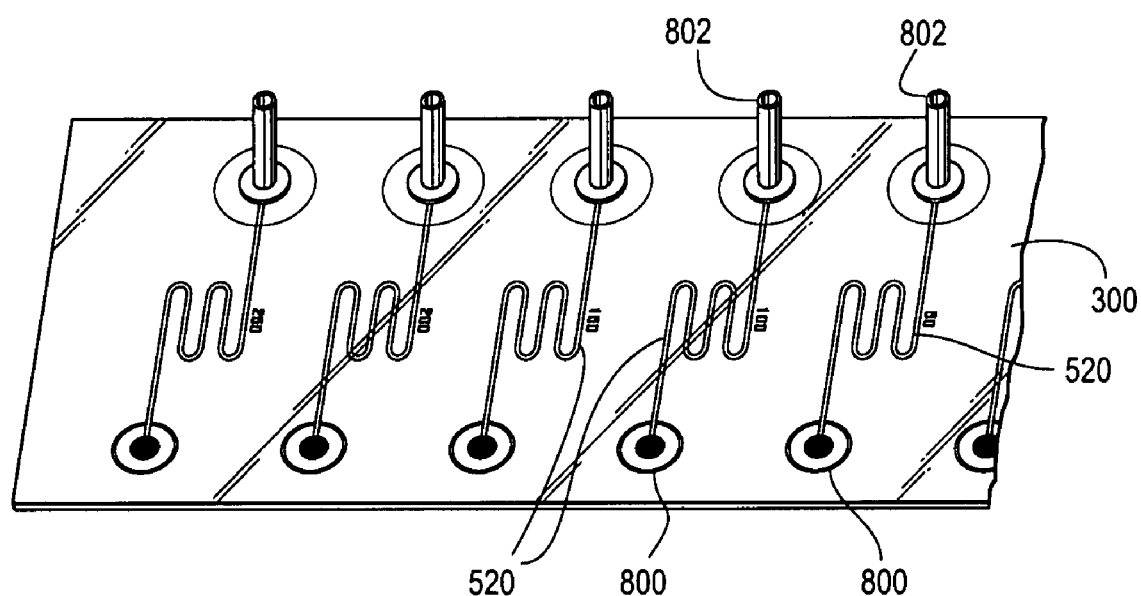
FIG. 8 is an illustration of a biosensor having integrated fluid containment structure (fluid flow channels) and photonic crystal sensor positioned within the fluid flow channels.

FIG. 8 is an illustration of a biosensor suitable for use in performing the experiments such as described above. The sensor 300 includes inlet ports 800 for introduction of a fluid sample. The sensor 300 features micron-scale fluid channels 520 each containing a photonic crystal sensor as described above. Outlet ports 802 are provided which connect to vacuum apparatus (not shown) or to pumps or injection devices allowing the sample to be drawn through the channels 520 and over the photonic crystal sensor incorporated therein. The photonic crystal sensor and the fluid channels are part of an integrated, monolithic structure which is fabricated using the molding process using the master template in the manner described previously.

Discussion

The fabrication and detection methods described in this work represent the building blocks that may be used to design and build more sophisticated lab-on-a-chip systems incorporating sensors for label-free biochemical or cellular analysis. This work demonstrates that a narrow photonic crystal region within a flow channel provides a strong resonant reflection signal, and that a large number of independent "pixels" may be monitored at one time within a small chip. The imaging capability may be utilized in several ways to improve the resolution and/or throughput of label-free measurements. As demonstrated with the serpentine flow channel design, a single "line" of PWV measurements across the width of many flow channels may be used to monitor biochemical binding in a large number of flow channels at one time. Although only "end point" measurements were shown here, a single PWV line may be scanned rapidly (~20 milliseconds per scan) to gather kinetic binding data for all the flow channels intersecting the line. Further, PWV measurements are not limited to a single reading across the width of a flow channel, but rather the variability in binding density from the center to the edge of the channel is easily detected.

These types of measurements will enable optimization of flow conditions and direct observation of edge effects that are not normally detected. Likewise, the serpentine flow channels allowed us to demonstrate detection of biochemical binding down the length of a single flow channel, where again rapid scanning will allow direct observation of immobilized ligand density binding variability and detected analyte variability, and any nonuniformity resulting from mass transport limitations. By taking many independent binding readings down the length of a channel, we expect to reduce the statistical (random) noise of individual PWV determinations to extremely low levels through averaging. In the case of our serpentine channel configuration, all the PWV shift readings, with >6000 readings within a single channel for ~22×22 $\mu m^2$ pixels, are easily gathered together to calculate an average PWV shift measurement for the entire channel.

The sensors of this disclosure allows reference channels to be incorporated in close physical proximity to active channels for highly accurate correction of temperature or buffer variability. Because active and reference regions are small, many reference regions may be easily incorporated onto a single chip.

The present disclosure also is compatible with more complex sensor/flow channel configurations that incorporate valving and mixing capabilities into the chip. This capability is useful not only for biochemical assays, but also for detection of immobilization of larger biological objects, including cells and bacteria for cytotoxicity assays, chemotaxis assays, and diagnostic tests, and cell/bacteria identification.

From the above disclosure, it will be appreciated that we have demonstrated in this example a single-step process for integrating the fabrication of photonic crystal biosensors and microfluidic channels. The process enables the submicron structure of the photonic crystal to be performed simultaneously with the >10 micron structures for the fluid channels, and self-aligns the photonic crystal sensors with the channels. The process can be performed using a room-temperature replica molding process that is performed on flexible plastic substrates for low-cost manufacturing. The fabricated sensors may be measured in a high-resolution imaging mode that can obtain information from many locations within the chip surface simultaneously for monitoring biochemical interactions in a high throughput manner and observation of binding interaction uniformity along the lengths and across the widths of the channels. We demonstrated the ability of the integrated sensors to detect changes in the bulk refractive index of fluid introduced into the channels, and to selectively detect an antibody at high concentration with an immobilized ligand. In the current work, flow was used to introduce reagents to the sensors in the channels. We demonstrate capabilities for applications in pharmaceutical compound screening, protein-protein interaction characterization, and cell-based assays using the presently described processes and structure upon incorporation of additional flow systems and elements.

EXAMPLE 2

Photonic Crystal Sensors with Fluid Containment Structures Having a Microplate Configuration Introduction The present disclosure also contemplates microplate sensor systems comprising arrays of microwells, each having individually addressed photonic crystal sensors. Microplate sensor systems of this aspect of the present disclosure may further comprise integral micron scale fluid containment structures (channels) for introducing fluid samples containing analytes into selected microwells.

Figure 9:
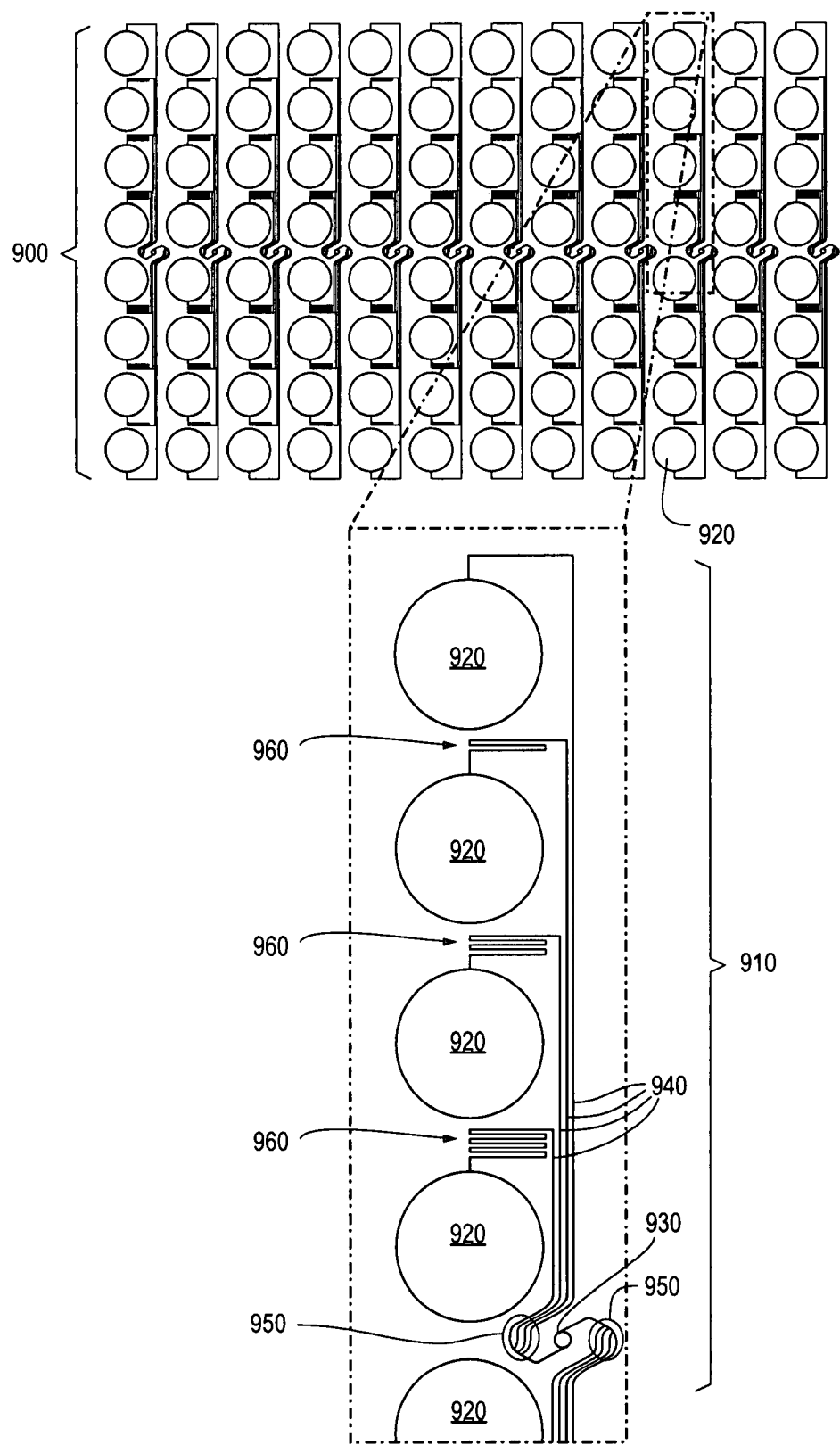
FIG. 9 is a top plan view of a microplate configuration for a biosensor having a fluid channel system for delivery of fluid samples to microwells having photonic crystal structures at the bottom thereof. The fluid channels also have photonic crystal sensors in the bottom surface of the fluid channels.

FIG. 9 is a schematic, top plan view of a microwell configuration 900 for a sensor system of this embodiment in the form of an array of 12×8 microwells 920. The sensor includes a fluid handling system 910 in the form of fluid channels 940 for delivery of fluid samples from ports 930 to the microwells 920. Each of the fluid channels 940 include photonic crystal sensors 950. The bottom surface of the microwells 920 include a photonic crystal sensor as shown the embodiment of FIG. 1A. The sensors 950 allow label-free measurements (referred to herein occasionally as "BIND" measurements) of the sample, whereas the photonic crystal sensors in the bottom of the microwells 920 allow measurements to be made after the sample flowing in the channels has been allowed to pass into the wells and interact with a second sample material added to the microwells. This possible use of the sensor will be described in detail below.

The inset in FIG. 9 provides an expanded view of a portion of one column of microwells and the corresponding fluid handling system 910. Features of this sensor include: (i) The eight microwells 920 in each column are attached to a common port 930 for both loading and waste; (ii) the photonic crystal sensors 950 in the channels associated with each of the eight wells are in substantial alignment, and all fall on the same horizontal line; (iii) The resistance (length) of the each channel 940 among the eight wells is identical, both between the microwell 920 and the photonic crystal sensor 950, and between the sensor 950 and the common port 930. This is achieved in the embodiment shown in FIG. 11 by use of serpentine channels 960 to add extra length as required to make the path length of the channels all the same.

Advantages of the system shown in FIG. 9 include (i) All the photonic crystal sensors 950 are aligned and in one row, therefore only one dimensional scanning required to make measurements of binding interactions in the sensors 950; (ii) Each channel 940 has the same length and fluid resistance, therefore the time for sample material to migrate to the sensors and to the microwells is the same for all the wells in a column of wells; (iii) eight common ports 930, one port per column of wells, means that eight different receptors (analytes) added to the wells can be tested in parallel.

Figure 10:
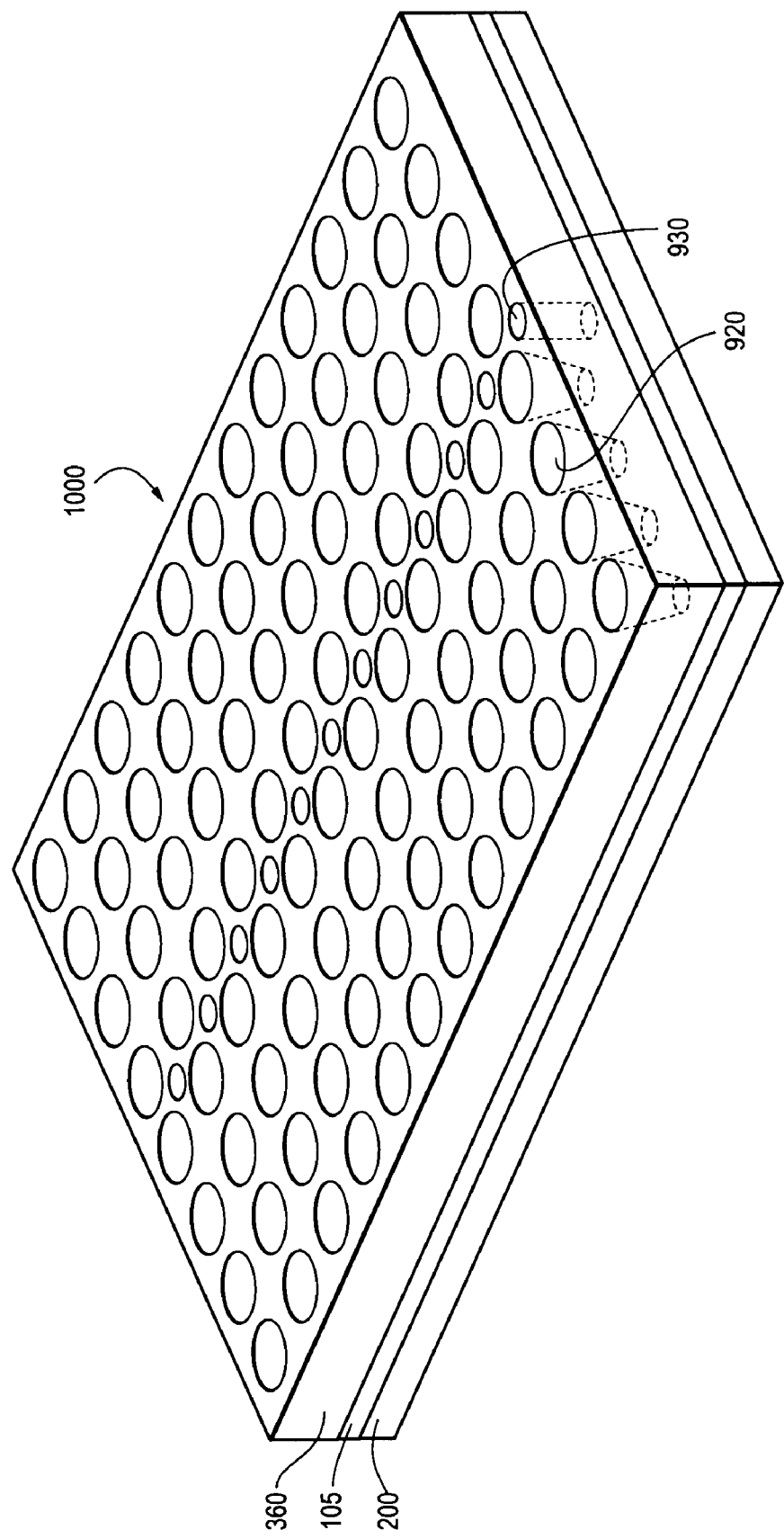
FIG. 10 is a perspective view of a plate configuration of a biosensor in the form of a microfluidic cartridge.

FIG. 10 provides a schematic diagram of a perspective view of a microwell configuration of this example in the form of a microfluidic cartridge 1000. As shown in this figure a PET supporting substrate layer 200 is provided which supports a patterned polymer layer 105 comprising a plurality of integrated fluid containment and photonic crystal structures. The sample wells 920 are tapered to minimize the fluid volume needed to fill them. An additional polycarbonate layer 360 is provided to enhance the volume capacity of the microwells and add structural integrity. (See the design of FIG. 1F).

Several device scenarios are contemplated for the embodiment of FIGS. 9 and 10, including:

Scenario A: The twelve common wells 930 are all filled with the same receptor protein, which enters all of the channels and binds to the photonic crystal BIND sensors placed in the channels 940 leading to the wells 920. Then, 96 unique analytes are loaded directly into the sample wells 920, and 96 assays are performed simultaneously using photonic crystal sensors contained in the sample wells 920. Alternatively, the user may wish to do twelve unique assays, one per column of wells, with eight repetitions for each assay.

Scenario B: The twelve common wells 930 are each filled with a different receptor protein, thereby labeling each column of eight wells 920 with a different protein. Then, eight unique analytes are introduced across the twelve rows, performing 96 simultaneous assays that test eight analytes versus twelve receptors.

Scenario C: Ninety six unique proteins are deposited in the sample wells 920 and allowed to bind to the photonic crystal sensors positioned in the bottom of the sample wells 920. One analyte is introduced into the twelve common wells 930 and allowed to flow into the wells 920. Ninety six unique assays are performed with the same analyte and different receptors.

The geometry can be changed so that the common wells (and the data readout) run in the other direction, allowing Scenario B to be reversed to twelve analytes versus eight receptors.

Figure 11:
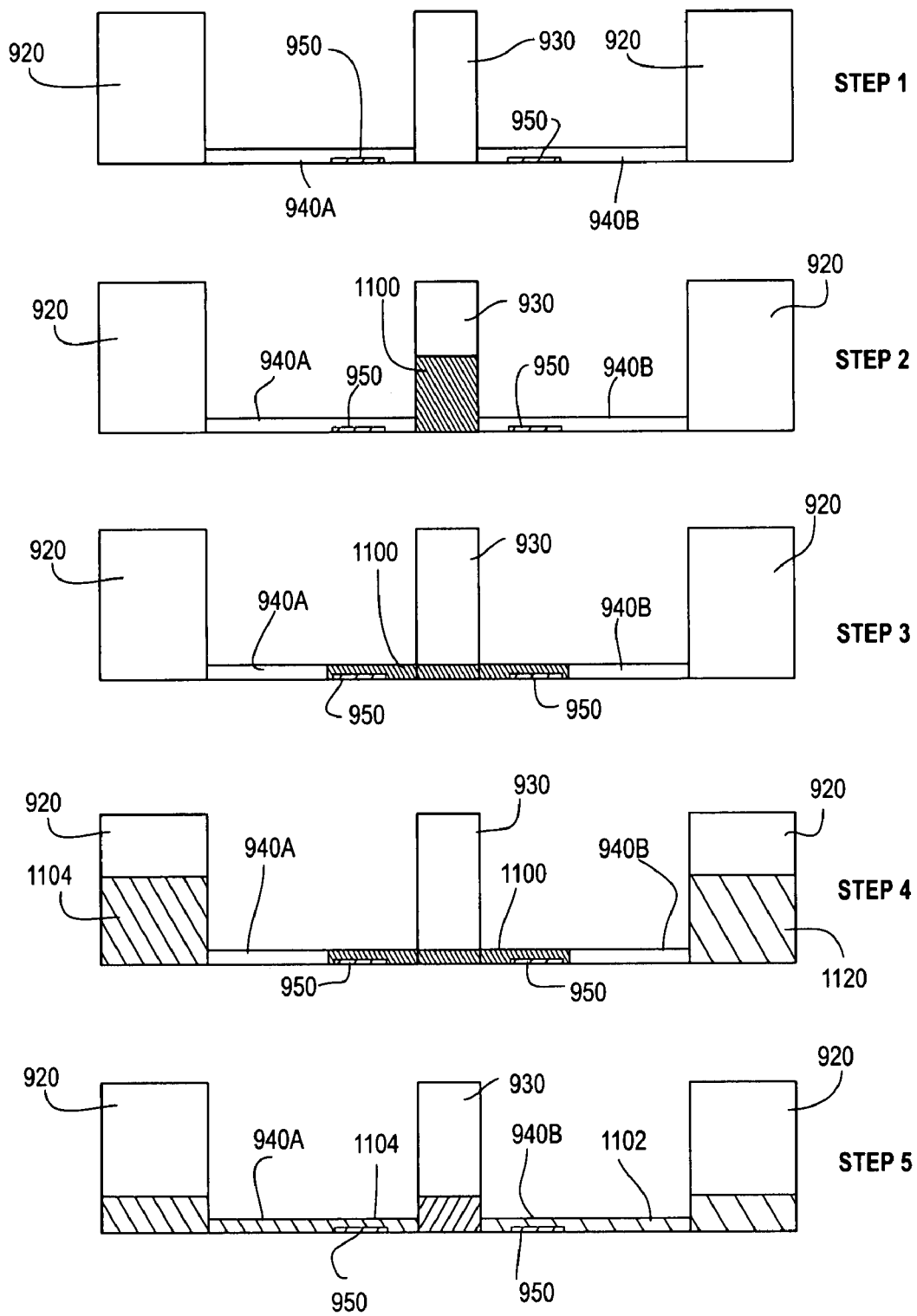
FIG. 11 is a schematic diagram illustrating the exemplary processing steps illustrating how the present sensor system can be used in one scenario using the biosensor of FIG. 10.

FIG. 11 provides a schematic diagram illustrating the exemplary processing steps illustrating how the present sensor system can be used in Scenario A of this Example. For simplicity, only one common well 930 and two sample wells 920 are shown in FIG. 11. Also note that the sample wells are not shown tapered, but use of tapered well is within the scope of this embodiment. The common well 930 is connected to the sample wells 920 via channels 940A and 940B, each having a photonic crystal sensor 950 positioned in the bottom surface of the channel 940A and 940B.

Step 1 shows the sensor system with the device empty. Step 2 shows the sensor system with receptor protein 1100 loaded into the common well 930. Step 3 shows receptor protein entering into channels 940A and 940B through hydrostatic pressure and capillary action. The fluid moves far enough to cover the photonic crystal sensors 950 but not much further. The device is designed so that fluid flow stops at the appropriate distance, in the channels 940 but past the photonic crystal sensors 950. Receptor molecules bind to the sensors 950 during this phase and a label free "BIND" PWV measurement is taken from the sensors 950 (e.g., using the instrument of FIG. 4). Step 4 shows the systems as two different analytes 1102 and 1104 are loaded into the sample wells 920. Step 5 shows the system as analytes 1102 and 1104 are pumped into channels 940A and 940B by hydrostatic pressure or vacuum until the height of the columns is equal in the sample wells 920 and the common well 930. This is designed so that sample flow proceeds past the sensors 950. The binding reactions between the analytes 1102 and 1104 and the receptor molecules bound to the photonic crystal sensor 950 starts and can be measured via PWV measurements in the manner described previously.

From the above discussion, it will be appreciated that we have described a photonic crystal biosensor (100, 300, 1000) with a fluid containment structure (e.g., channels 940, or wells 130 or 920) having a cavity (well or channel), integrated with a photonic crystal sensor (120/950) comprising a periodic surface grating structure formed in the internal surface or cavity of the fluid containment structure, as shown in the drawings, wherein the fluid containment structure and periodic surface grating structure of the photonic crystal structure comprise a integral, monolithic structure.

As shown in FIG. 1A, the integral, monolithic structure may take the form of an an integral polymer structure comprising an optically clear substrate layer 200, a cured polymer layer 105, and a relatively high index of refraction material 180 deposited on the cured polymer layer 105.

As shown for example in FIGS. 9 and 11, the sensor may includes a cavity in the form a sample well 920, and wherein the integral monolithic structure further comprises a port 930 for receiving the fluid sample, a channel 940 having a surface and providing a fluid path for connecting the port 930 to the micron-scale fluid containment structure 920, and a second photonic crystal structure 950 comprising a periodic surface grating structure formed in the surface of the channel.

In the above embodiments, the sensor may include a target material which is bound to the periodic grating structure of the photonic crystal structure, with the target material exposed within the fluid containment structure (well or channel) for binding of an analyte. Examples of the target material include proteins, peptides, DNA molecules, RNA molecules, oligonucleotides, lipids, carbohydrates, polysaccharides; glycoproteins, lipoproteins, sugars, cells, bacteria, virus, and candidate molecules.

Glossary

"Polymer" refers to a molecule comprising a plurality of repeating chemical groups, typically referred to as monomers. Polymers are often characterized by high molecular masses. Polymers useable in the present disclosure may be organic polymers or inorganic polymers and may be in amorphous, semi-amorphous, crystalline or partially crystalline states. Polymers may comprise monomers having the same chemical composition or may comprise a plurality of monomers having different chemical compositions, such as a copolymer. Cross linked polymers having linked monomer chains are particularly useful for some applications of the present disclosure. Polymers useable in the methods, devices and device components of the present disclosure include, but are not limited to, plastics, thermoplastics, elastomers, elastoplastics, thermostats, and acrylates. Exemplary polymers include, but are not limited to, polymethylmethacrylate, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, polymethylpentene, polyphenylene oxides and polyphenylene sulfides, polyphthalamide, polypropylene, polyurethanes, styrenic resins, sulphone based resins, vinyl-based resins or any combinations of these.

The term "electromagnetic radiation" and "light" are used synonymously in the present description and refer to waves of electric and magnetic fields. Electromagnetic radiation useful for the methods of the present disclosure includes, but is not limited to ultraviolet light, visible light, infrared light, microwaves, radio waves or any combination of these.

"Optical communication" refers to a configuration of two or more elements wherein one or more beams of electromagnetic radiation are capable of propagating from one element to the other element. Elements in optical communication may be in direct optical communication or indirect optical communication.

"Direct optical communication" refers to a configuration of two or more elements wherein one or more beams of electromagnetic radiation propagate directly from a first device element to another without use of optical components for steering and/or combining the beams. "Indirect optical communication" on the other hand refers to a configuration of two or more elements wherein one or more beams of electromagnetic radiation propagate between two elements via one or more device components including, but not limited to, wave guides, fiber optic elements, reflectors, filters, prisms, lenses, gratings and any combination of these device components.

"Thin film" refers to a coating or layer of atoms, molecules or ions or mixtures and/or clusters thereof. Thin films in the present disclosure may comprise a single-layer having a substantially constant composition, a single-layer having a composition which varies as a function of physical thickness or a plurality of thin films layers. Thin film layers of the present disclosure include but are not limited dielectric materials, semiconductors, conducting materials, organic materials such as polymers and any combinations of these materials. In a preferred embodiment, reference to thin dielectric films in the present disclosure includes but is not limited to metal oxide, metalloid oxide and salt thin films. Thin film layers of the present disclosure may have any size, shape, physical thickness or optical thickness suitable for a selected application.

The terms "frequency distribution of a photonic band gap" and "reflectance spectrum of a photonic band gap" are used synonymously in the present description and refer to the frequencies of incident electromagnetic radiation that transmission through a photonic crystal is at least partially prevented. The present disclosure provides dynamic photonic crystals having a tunable photonic band gap wherein the frequency distribution of the photonic band gap may be selectively adjusted by exposure of the crystal to polarized excitation electromagnetic radiation.

As used herein, "nanosized" refer to features having at least one physical dimension (e.g. height, width, length, diameter etc.) ranging from a few nanometers to a micron, including in the range of tens of nanometers to hundreds of nanometers. In an embodiment, a nanosized feature is structure, relief feature or relief feature having at least one physical dimension that is on the order of hundreds of nanometer. For example, the width and/or height of a nanosized feature can be on the order of 10's to 100's of nm and the length of a nanosized feature of can be on the order of microns to 1000's of microns.

As used herein, "micron-sized" refer to features having at least one physical dimension (e.g. height, width, length, diameter etc.) ranging from a micron to a thousand microns, including in the range of tens of microns to hundreds of microns. In an embodiment, a micron-sized feature is a structure having at least one physical dimension ranging from about 1 micron to about 1000 microns. For example, the width and/or height of a microsized feature can be on the order of 10's to 100's of microns and the length of a microsized feature of can be on the order of millimeters to centimeters.

As used herein the term "fluid" refers to a material that is capable of flow and conforms, at least partially, to the outline of its container. Fluids in the present disclosure include liquids, gases, solutions, colloids (e.g., aerosols, emulsions, gels and foams) and any combinations and mixtures of these. "Polymer layer" refers to a layer that comprises one or more polymers. Polymer layers useful in the present disclosure may comprise a substantially pure polymer layer or a layer comprising a mixture of a plurality of different polymers. Polymer layers useful in the present disclosure also include multiphase polymeric layers and/or composite polymeric layers comprising a combination of one or more polymer and one or more additional material, such as a dopant or structural additive.

"Candidate molecules" include therapeutic candidate molecules which are molecules that may have some effect on a biological process or series of biological processes when administered to a human, other animal or plant subject. Therapeutic candidate molecules include, but are not limited to, drugs, pharmaceuticals, potential drug candidates and metabolites of drugs, biological therapeutics, potential biological therapeutic candidates and metabolites of biological therapeutics, organic, inorganic and/or hybrid organic inorganic molecules that interact with one or more biomolecules, molecules that inhibit, decrease or increase the bioactivity of a biomolecule, inhibitors, ligands and derivatives, variants and complexes of these.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Separate embodiments of the disclosure are also intended to be encompassed wherein the terms "comprising" or "comprise(s)" or "comprised" are optionally replaced with the terms, analogous in grammar, e.g.; "consisting/consist(s)" or "consisting essentially of/consist(s) essentially of" to thereby describe further embodiments that are not necessarily coextensive.

The disclosure has been described with reference to various specific and preferred embodiments and techniques. However, it should be understood that many variations and modifications may be made while remaining within the spirit and scope of the disclosure. It will be apparent to one of ordinary skill in the art that compositions, methods, devices, device elements, materials, procedures and techniques other than those specifically described herein can be applied to the practice of the disclosure as broadly disclosed herein without resort to undue experimentation. All art-known functional equivalents of compositions, methods, devices, device elements, materials, procedures and techniques described herein are intended to be encompassed by this disclosure. This disclosure is not to be limited by the embodiments disclosed, including any shown in the drawings or exemplified in the specification, which are given by way of example or illustration and not of limitation. All questions concerning scope of the disclosure are to be answered by reference to the appended claims.

We claim:

1. A method of making a photonic crystal sensor having an integrated fluid containment structure, said method comprising the steps of:

providing a master template having an external surface with a pattern comprising a photonic crystal periodic surface grating structure and structure for forming a fluid containment structure, the periodic surface grating structure located within the structure forming the fluid containment structure;

transferring the pattern of said master template to a material such that the material forms a fluid containment structure having a cavity with the photonic crystal periodic surface grating structure positioned within the cavity; and depositing a thin dielectric film on the photonic crystal periodic surface grating structure to thereby forming a photonic crystal sensor.

2. The method of claim 1, wherein the cavity comprises a sample well.

3. The method of claim 1, wherein the cavity comprises a fluid flow channel.

4. The method of claim 1, wherein said step of transferring is carried out via replica molding.

5. The method of claim 1 wherein said step of transferring is carried out via imprint lithography.

6. The method of claim 1 wherein said material comprises a curable fluid material, and wherein said step of transferring comprises the steps of:

contacting said external surface of said master template with the curable fluid material, wherein said curable fluid material conforms to the shape of the external surface of the master template;

curing said curable fluid material while in contact with the external surface of the master template; and separating the cured fluid material from the master template.

7. The method of claim 1, wherein the external surface of the master template is configured to form a plurality of sample wells, at least one port, and fluid channels connecting the port to the sample wells, and wherein the external surface is patterned to form a photonic crystal periodic surface grating in at least one of 1) each of the fluid channels, and 2) each of the sample wells.

* * * * *